(12) United States Patent
Diec et al.

(10) Patent No.: US 6,468,551 B1
(45) Date of Patent: Oct. 22, 2002

(54) COSMETIC OR DERMATOLOGICAL PREPARATIONS BASED ON EMULSIFIERS WHICH ARE FREE FROM ETHYLENE OXIDE AND PROPYLENE OXIDE, FOR THE PREPARATION OF MICROEMULSION GELS

(75) Inventors: Khiet Hien Diec, Hamburg (DE); Wolfgang Meier, Basel (CH); Jörg Schreiber, Hamburg (DE)

(73) Assignee: Beiersdorf AG, Hamburg (DE)

( * ) Notice: Subject to any disclaimer, the term of this patent is extended or adjusted under 35 U.S.C. 154(b) by 0 days.

(21) Appl. No.: 09/269,778

(22) PCT Filed: Oct. 9, 1997

(86) PCT No.: PCT/EP97/05553

§ 371 (c)(1),
(2), (4) Date: Jun. 18, 1999

(87) PCT Pub. No.: WO98/15255

PCT Pub. Date: Apr. 16, 1998

(30) Foreign Application Priority Data

Oct. 10, 1996 (DE) .......................... 196 41 672

(51) Int. Cl.[7] .............. A61K 7/00; A61K 7/48
(52) U.S. Cl. ............ 424/401; 424/70.1; 424/59; 424/47; 424/450; 514/844; 514/846
(58) Field of Search .............. 424/401, 47, 59, 424/70.1, 450; 514/944, 844, 846, 937

(56) References Cited

U.S. PATENT DOCUMENTS 5,399,652 A * 3/1995 Bindle et al. ............. 528/26
5,753,241 A * 5/1998 Ribier et al. ............. 424/401
6,004,580 A * 12/1999 Backlund et al. ........... 424/450

FOREIGN PATENT DOCUMENTS

| EP | 0 278 660 | * | 2/1988 |
| EP | 0 728 460 | * | 1/1996 |

* cited by examiner

Primary Examiner—Diana Dudash
Assistant Examiner—M. Haghighatian
(74) Attorney, Agent, or Firm—Norris McLaughlin & Marcus

(57) ABSTRACT

Microemulsion gels a) based on oil in water type, comprising an oil phase, substantially consisting of not easily volatile constituents, and an aqueous phase containing one or more O/W emulsifiers free from ethylene oxide and propylene oxide and possibly one or more additional O/W emulsifiers, an emulsifier content which is lower than 20 wt. % related to the full weight of the microemulsion, obtained in such a way that a mixture of basic constituents, consisting of an aqueous phase, an oil phase, one or more O/W emulsifiers, possibly one or more additional O/W emulsifiers, possibly other auxiliary, additional or active agents, is made to react against each other in a mixing ratio so that a microemulsion can be obtained and b) in which droplets of discontinuous oil phase are bound to each other by one or more cross-linking substances, whose molecules are characterized by at least one hydrophylic area having a suitable expansion for bridging of distance between each microemulsion droplet and at least one hydropobic area, which can interact hydrophobically with the microemulsion droplets.

7 Claims, No Drawings

COSMETIC OR DERMATOLOGICAL PREPARATIONS BASED ON EMULSIFIERS WHICH ARE FREE FROM ETHYLENE OXIDE AND PROPYLENE OXIDE, FOR THE PREPARATION OF MICROEMULSION GELS

The present invention relates to microemulsion gels of the oil-in-water type, to a process for their preparation and to their use for cosmetic purposes, in particular for topical use.

As a particular embodiment, the present invention relates to the use of microemulsion gels according to the invention for medical purposes, in particular as medicament carriers for lipophilic active compounds and their pharmaceutical use as topical dermatological agents, but also for the parenteral administration of pharmaceutical active compounds and for parenteral nutrition.

Cosmetic skin care is primarily to be understood as meaning that the natural function of the skin as a barrier against environmental influences (for example dirt, chemicals and microorganisms) and against the loss of endogenous substances (for example water, natural fats and electrolytes) is intensified or re-established.

If this function is impaired, increased absorption of toxic or allergenic substances or attack by microorganisms and as a consequence toxic or allergic skin reactions may occur.

The aim of skin care is furthermore to compensate the loss of fats and water from the skin caused by daily washing. This is important particularly if the natural capacity for regeneration is inadequate. Skin-care products should furthermore protect against environmental influences, in particular against the sun and wind, and delay skin ageing.

Medical topical compositions as a rule comprise one or more medicaments in an active concentration. For simplicity, reference is made to the legal provisions of the Federal Republic of Germany (for example cosmetics legislation, legislation on foodstuffs and medicaments) for a clear distinction between cosmetic and medical use and corresponding products.

Gels are customary cosmetic and dermatological formulation forms which have become more and more widespread particularly in recent times.

In the technical sense, gels are understood as meaning: relatively dimensionally stable, easily deformable disperse systems of at least two components, which as a rule comprise a—usually solid—colloidally divided substance of long-chain molecular groupings (for example gelatin, silicic acid or polysaccharides) as structuring agents and a liquid dispersant (for example water). The colloidally divided substance is often called a thickener or gelling agent. It forms a three-dimensional network in the dispersant, it being possible for individual particles present in colloidal form to be linked to one another more or less firmly via electrostatic interaction. The dispersant, which surrounds the network, is distinguished by electrostatic affinity for the gelling agent, i.e. a predominantly polar (in particular: hydrophilic) gelling agent preferably gels a polar dispersant (in particular: water), whereas a predominantly non-polar gelling agent preferably gels non-polar dispersants.

Strong electrostatic interactions, which are realized, for example, in hydrogen bridge bonds between the gelling agent and dispersant, but also between dispersant molecules with one another, can lead to a high degree of crosslinking of the dispersant as well. Hydrogels can comprise water to the extent of almost 100% (alongside, for example, about 0.2–1.0% of a gelling agent), and at the same time have an entirely solid consistency. The water content is present here in ice-like structural elements, so that gels entirely justify the origin of their name [from lat. "gelatum"="frozen" via the alchemistic term "gelatina" (16th century) for the modem term "gelatin"].

Lipogels and oleogels (of waxes, fats and fatty oils) as well as carbogels (from paraffin or petrolatum) are furthermore also customary in cosmetic and pharmaceutical galenics. In practice, a distinction is made between oleogels, which are in virtually anhydrous form, hydrogels, which are practically fat-free, and oil/water gels which are based on O/W or W/O emulsions which, additionally, however, also have features of a gel structure. Gels are usually transparent. In cosmetic and pharmaceutical galenics, gels are as a general rule distinguished by a semi-solid, often free-flowing consistency.

In simple emulsions, in the one phase, finely disperse droplets of the second phase (water droplets in W/O or lipid vesicles in O/W emulsions) enclosed by an emulsifier shell are present. The droplet diameters of the usual emulsions are in the range from about 1 $\mu$m to about 50 $\mu$m. Without further colouring additives, such "macroemulsions" are milky white in colour and opaque. Finer "macroemulsions", the droplet diameters of which are in the range from about $10^{-1}$ $\mu$m to about 1 $\mu$m, again without colouring additives, are bluish-white in colour and non-transparent.

Only micellar and molecular solutions having particle diameters of less than about $10^{-2}$ $\mu$m appear clear and transparent.

The droplet diameter of transparent or translucent microemulsions, on the other hand, is in the range from about $10^{-2}$ $\mu$m to about $10^{-1}$ $\mu$m. Such microemulsions usually have a low viscosity. The viscosity of many microemulsions of the O/W type is comparable to that of water.

Surfactant gels are furthermore customary formulations of the prior art. These are understood as being systems which, in addition to water, have a high concentration of emulsifiers, typically more than about 25% by weight, based on the total composition. If oil components are solubilized in these surfactant gels, which is their technical name, microemulsion gels, which are also called "ringing gels", are obtained. Cosmetically more elegant microemulsion gels can be obtained by addition of nonionic emulsifiers, for example alkyl polyglycosides. Here also, the high content of emulsifiers is a disadvantage.

An advantage of microemulsion gels is that active compounds can be present in finely disperse form in the disperse phase. Another advantage is that, because of their low viscosity, they can be sprayed. When microemulsions are used as cosmetics, corresponding products are distinguished by a high cosmetic elegance.

It is known per se to link the droplets of a low-viscosity, in particular thinly liquid microemulsion with crosslinking substances with one another, in order to obtain the three-dimensional network of a gel in this manner.

Chain-like, hydrophilic molecules which contain a hydrophobic radical on each of the two chain ends are described in Nachr. Chem. Techn. Lab. 43 (1995) No. 1, page 9 et seq. for crosslinking microemulsion droplets. Those hydrophobic radicals are immersed in the microemulsion droplets, the hydrophilic chain regions being in the continuous aqueous phase. In the strict sense, it is certainly not necessary for the hydrophobic radicals to be "immersed". In individual cases, it can also be entirely sufficient if the hydrophobic radicals come into contact with the surface of the microemulsion droplets by hydrophobic interaction and remain stuck to this more or less firmly.

In the above literature reference, the crosslinkers are poly-oxyethylene glycols with oleyl groups as hydrophobic end groups.

A disadvantage of microemulsions, and therefore also of the microemulsion gels of the prior art, is that a high content of one or more emulsifiers must always be employed, since the low droplet size results in a high interface between the phases, which as a rule must be stabilized by emulsifiers.

Although the use of the customary cosmetic emulsifiers is acceptable per se, emulsifiers, like any chemical substance ultimately, can in certain circumstances cause allergic reactions or reactions based on hypersensitivity of the user.

It is thus known that particular photodermatoses are induced by certain emulsifiers, and also by various fats, and simultaneous exposure to sunlight. Such photodermatoses are also called "Majorca acne". An object of the present invention was therefore to develop sunscreen products.

As particular embodiments, the present invention thus relates to cosmetic and dermatological light protection formulations, in particular skin-care cosmetic and dermatological light protection formulations.

The damaging effect of the ultraviolet part of solar radiation on the skin is generally known. While rays having a wavelength of less than 290 nm (the UVC range) are absorbed by the ozone layer in the Earth's atmosphere, rays in the range between 290 nm and 320 nm, the UVB range, cause erythema, simple sunburn or even actual burns of greater or lesser severity.

The narrower range around 308 nm is seen as the erythema activity maximum of sunlight.

Numerous compounds are known for protection against UVB radiation, these usually being derivatives of 3-benzylidenecamphor, of 4-aminobenzoic acid, of cinnamic acid, of salicylic acid, of benzophenone and also of 2-phenylbenzimidazole.

For the range between about 320 nm and about 400 nm, the UVA range, it is also important to have available filter substances, since the rays thereof can also cause damage. It has thus been proved that UVA radiation leads to damage to the elastic and collagenic fibres of connective tissue, which makes the skin age prematurely, and that it has to be regarded as a cause of numerous phototoxic and photoallergic reactions. The damaging effect of UVB radiation can be intensified by UVA radiation.

However, UV radiation can also lead to photochemical reactions, the photochemical reaction products then intervening in the skin metabolism.

To prevent these reactions, antioxidants and/or free-radical scavengers can additionally be incorporated into the cosmetic or dermatological formulations.

Most inorganic pigments, which are known to be used in cosmetics for protecting the skin against UV rays, are UV absorbers or UV reflectors. These pigments are oxides of titanium, zinc, iron, zirconium, silicon, manganese, aluminium and cerium, and mixtures thereof, as well as modifications.

Microemulsion gels are also suitable for other cosmetic dermatological uses, for example deodorants, so that in a particular embodiment, the present invention relates to microemulsion gels as a base for cosmetic deodorants.

Cosmetic deodorants serve to eliminate body odour, which develops when fresh perspiration, which is odourless per se, is decomposed by microorganisms. The customary cosmetic deodorants are based on various activity principles.

In antiperspirants, the formation of perspiration can be reduced by astringents—chiefly aluminium salts, such as aluminium hydroxychloride (hydrated aluminium chloride).

By using antimicrobial substances in cosmetic deodorants, the bacterial flora on the skin can be reduced. In the ideal case, only the odour-causing microorganisms should be effectively reduced here. The flow of perspiration itself is not influenced as a result, and in the ideal case only the microbial decomposition of the perspiration is temporarily stopped.

Combination of astringents with antimicrobially active substances in one and the same composition is also customary.

Deodorants should meet the following conditions:
1) They should cause reliable deodorization.
2) The natural biological processes of the skin must not be impaired by the deodorants.
3) The deodorants must be harmless in the event of an overdose or if used other than as specified.
4) They should not become concentrated on the skin after repeated use.
5) They should be easy to incorporate into customary cosmetic formulations.

Both liquid deodorants, for example aerosol sprays, roll-ons and the like, and solid formulations, for example deodorant sticks, powders, powder sprays, intimate cleansing compositions and the like, are known and customary.

The use of microemulsions as a base for formulations having a deodorizing or antiperspirant action is also known. Their relatively high content of emulsifiers with the disadvantages described has to date been a poor state of affairs which was to be remedied.

Another object of the present invention was thus to develop formulations which are suitable as a base for cosmetic deodorants or antiperspirants and do not have the disadvantages of the prior art.

It was furthermore an object of the invention to develop cosmetic bases for cosmetic deodorants which are distinguished by a good skin tolerability.

It was furthermore an object of the present invention to provide products based on microemulsion gels with the broadest possible diversity of uses. For example, bases for formulation forms such as cleansing emulsions, face- and body-care formulations, and also distinctly medical/pharmaceutical presentation forms, for example formulations against acne and other skin manifestations, were to be provided.

In a particular embodiment, the invention therefore relates to cleansing emulsions, in particular facial cleansing emulsions, preferably make-up removers, for example eye make-up removers.

Such formulations are known per se. They are usually mixtures of cosmetic oils or aqueous formulations of surface-active substances, the function of which is to solubilize the contamination or the make-up particles and remove them from the skin.

Waterproof eye make-up, for example mascara, can only be removed satisfactorily with water-based make-up removers which contain special surfactants. However, these surfactants often have only limited physiological tolerability. When such substances come into contact with the mucous membrane, in particular the mucous membrane of the eye, these substances lead to irritation, which manifests itself, for example, in a reddening of the eyes. Reactions of this type are typical of surfactant-containing products.

An object of the present invention was consequently to provide a remedy for such problems.

In another embodiment, the present invention relates to hair cosmetics formulations. In particular, the present invention relates to hair cosmetics formulations for care of the hair and the scalp. In a preferred embodiment, the present invention relates to formulations which serve to strengthen the individual hairs and/or to impart hold and body to the hairstyle overall.

Roughly speaking, human hair can be divided into the living part, the hair root, and the dead part, the hair shaft. The hair shaft in turn comprises the medulla, which nevertheless through evolution has become insignificant for modern man and has receded, and in the case of thin hair is often absent entirely, and furthermore the cortex which surrounds the medulla and the cuticula which encloses the entirety of the medulla and cortex.

The cuticula in particular, but also the keratinous region between the cuticula and cortex, as the outer shell of the hair, are exposed to particular demands due to environmental influences, due to combing and brushing, and also due to hair treatment, in particular colouring of the hair and deforming of the hair, for example permanent wave processes.

When exposed to particularly aggressive demands, for example bleaching with oxidizing agents, such as hydrogen peroxide, in which the pigments distributed in the cortex are destroyed by oxidation; the inside of the hair can also be affected. If human hair is to be coloured permanently, in practice only oxidizing hair-colouring processes are possible. In the case of oxidative colouring of the hair, the dyestuff chromophores are formed by reaction of precursors (phenols, aminophenols and less frequently also diamines) and bases (usually p-phenylenediamine) with the oxidizing agent, usually hydrogen peroxide. Hydrogen peroxide concentrations of about 6% are usually used for this.

The process is usually based on a bleaching action by the hydrogen peroxide taking place, in addition to the colouring action. In human hair coloured by oxidation, as with bleached hair, microscopic holes are detectable at the points where melanin granules were present. It is a fact that the oxidizing agent hydrogen peroxide can react not only with the colour precursors but also with the hair substance and as a result under certain circumstances can cause damage to the hair.

Washing the hair with aggressive surfactants can also make demands on the hair, and at least reduce its appearance or the appearance of the hairstyle overall. For example, certain water-soluble hair constituents (for example urea, uric acid, xanthine, keratin, glycogen, citric acid and lactic acid) can be leached out by washing the hair.

For these reasons, in some cases hair-care cosmetics which are intended to be rinsed out of the hair again after their action and in some cases those which are to remain on the hair have been used for a relatively long time. The latter can be formulated such that they not only care for the individual hair, but also improve the appearance of the hairstyle overall, for example by imparting to the hair more body, fixing the hairstyle over a longer period of time or improving its ease of styling.

For example, the combability of hair can be improved decisively by quaternary ammonium compounds. Such compounds are absorbed onto the hair and are often still detectable on the hair after the hair has been washed several times.

However, the prior art has lacked active compounds and formulations which satisfactorily provide care for damaged hair. Formulations which should give the hairstyle body have also often proved to be inadequate, or at least they were unsuitable for use as hair-care formulations. Formulations of the prior art which fix the hairstyle as a rule comprise, for example, viscous constituents, which run the risk of giving rise to a feeling of tackiness, which often has to be compensated by skilful formulation.

An object was therefore to also remedy the disadvantages of the prior art.

A particular object of the present invention was to provide gelatinous formulations based on finely disperse systems of the oil-in-water type with the lowest possible emulsifier content which do not have the disadvantages of the prior art and which can have the most diverse cosmetic and/or dermatological applications, for example the uses described above. Another object of the invention was to enrich the limited range of gelatinous preparations based on finely disperse systems of the oil-in-water type of the prior art.

In the laid-open Specification WO 96/28132 microemulsion gels are prepared using O/W emulsifiers which contain ethylene oxide, which are mixed with suitable W/O emulsifiers and an oily phase.

The gels are prepared using crosslinker substances by subjecting the mixture to phase inversion, for example at elevated temperature, and cooling it to room temperature. This reference further describes that the crosslinking of the oil droplets or the preparation of the microemulsion gels also takes place without phase inversion.

Prior art microemulsions prepared in this way do, however, have the disadvantage that the process is based on emulsifiers which contain ethylene oxide. From an ecological viewpoint and the known fact that EO-containing emulsifiers can be poorly tolerated by the skin as a result of impurities from the preparation process, the aim was to overcome these prior art disadvantages.

It is known per se to prepare low-viscosity microemulsions without these emulsifiers which contain ethylene oxide. DE 4417476 A1 describes microemulsions containing alkyl polyglycosides (Plantaren 1200), which contain fatty acid polyol partial esters as coemulsifiers. This reference also describes alkyl polyglycoside/ethylene-oxide-containing emulsifier mixtures which are able to solubilize hydrocarbons. As is known, the transparency of the microemulsions is greatest when the droplet size is kept below 100 nm (see Table III, Example 16).

A disadvantage here is that exclusively hydrocarbons are suitable for the preparation of APG-containing microemulsions.

An explanation of this fact can be found in a publication in Colloid & Polymer Science 273: 1995, p. 565 ff. Relatively polar oils as hydro-carbons lead to the alkyl polyglycosides migrating from the oil/water interface. Since only the emulsifiers present at the interface can bring about a reduction in the oil/water interfacial tension to values around 0 $mN/m^{-1}$, hydrocarbons are thus preferably used as oil components for the preparation of APG-containing microemulsions.

In addition, DE 4411557 A1 describes inter alia low-viscosity microemulsions which consist of a mixture of ethylene-oxide-containing nonionic and anionic surfactants (ceteth-5/oleth-5; lauryl ether-2 sulphate). Low-viscosity microemulsions for oral applications based on lecithin/ethanol/propylene glycol are described in WO 92/02207. The thickening to give the microemulsion gel is induced using gelatin as a water-soluble polymer. A disadvantage for cosmetic applications is the lack of a cosmetic oily phase. In addition, the novel principle of crosslinking oil droplets using hydrophobically modified water-soluble polymers is not applied.

Lecithin gels are described in the literature (J. Phys. Chem. 92, 1988, 829; Colloid Polymer Science 268, 1990, 356). These gels are obtained by adding small amounts of water to a mixture of an organic solvent and lecithin. When water is added, the inverse micelles form cylindrical, water-solubilizing structures, become entangled with one another and thus explain the high viscosity of these mixtures. (Colloid Poly. Sci. 268, 1990, 356). The use of ethanol as an amphiphilic cosolvent for the preparation of lecithin-containing microemulsions and the gelling with polysaccharides such as gelatin or agar is described in WO 95/31969. The novel principle of crosslinking microemulsion droplets using hydrophobically modified water-soluble polymers is not discussed. Neither is it described that the addition of a coemulsifier of the oil-in-water type to a lecithin/oil mixture with the addition of water, with exploitation of an intermediate viscous gel state, gives, upon the addition of further water, novel oil-in-water microemulsions or, in the presence of novel crosslinkers, novel oil-in-water microemulsion gels. It was also hitherto unknown in the prior art how at least a certain proportion of free cells present in body fluids or, where appropriate, also cells which occur in a greater or lesser agglomerated form are able to be linked with one another, as a result of which the body fluid in question could undergo an increase in viscosity. When the human or animal body is wounded, a greater or lesser amount of blood firstly escapes, the coagulation of which plays an important role in the healing of the wound. Before coagulation, the blood is however of low viscosity, meaning that the blood flow merely weakens the body as a result of hypovolemia, but does not contribute to wound healing. It would be desirable to assist the blood locally, i.e. extracorporeally in increasing its viscosity in order to prevent a hypovolemia which, moreover, especially in the case of wounds which bleed heavily, can lead to the life-threatening condition of hypovolemic shock.

In addition, it was unknown that, for example, emulsifiers based on acyl lactylates and acyl glutamates or else nonionic ethylene-oxide-free emulsifiers are suitable, in the presence of suitable ethylene-oxide-free coemulsifiers and/or lecithin, for giving transparent microemulsion gels. By contrast, acyl lactylates as emulsifiers for macroemulsions are known (Food Prod. Developm. 6, 1972, 80–84; WO 88/06880, DE 4412081). In addition, the specifications WO 95/05799 and EP 573253 also describe that, for example, acyl lactylates may have antibacterial effectiveness or are advantageous in other ways (WO 95/05153; U.S. Pat. No. 3,472,940; EP 586234).

In summary, the object of the present invention was to make available ethylene-oxide-free and propylene-oxide-free emulsifiers in low concentration for the preparation of transparent/translucent microemulsions and microemulsion gels having a relatively broad variation possibility of cosmetic oil components. In addition, the object of the present invention was to use emulsifiers or polymers which, in addition to their property of being able to reduce interfacial tension or of being able to thicken the microemulsion to give a gel, can additionally achieve a physiological action.

Surprisingly, all of the objects on which the invention is based are achieved by microemulsion gels (a) based on microemulsions of the oil-in-water type, which comprise an oily phase, which is essentially composed of constituents of low volatility, and an aqueous phase comprising: one or more O/W emulsifiers which is/are free from ethylene oxide and propylene oxide and if desired furthermore comprising one or more W/O emulsifiers having an emulsifier content of less than 20% by weight, based on the total weight of the microemulsion, obtainable by formulating a mixture of the base components, comprising the aqueous phase, the oily phase, one or more of the O/W emulsifiers according to the invention, if desired one or more W/O emulsifiers, and if desired further auxiliaries, additives and/or active compounds, in a defined mixing ratio to one another to give a microemulsion, (b) in which the droplets of the discontinuous oily phase are joined to one another by one or more crosslinking substances, the molecules of which are distinguished by at least one hydrophilic region, which has an extension which is suitable for bridging the distance between the microemulsion droplets, and by at least one hydrophobic region, which is capable of entering into a hydrophobic interaction with the microemulsion droplets.

Surprisingly, all of the objects on which the invention is based are furthermore solved by microemulsion gels (a) based on microemulsions of the oil-in-water type, which comprise an oily phase, which is essentially composed of constituents of low volatility, comprising: one or more O/W emulsifiers which is/are free from ethylene oxide and propylene oxide, and lecithin or lecithin derivatives and if desired furthermore comprising one or more W/O emulsifiers having an emulsifier content of less than 20% by weight, based on the total weight of the microemulsion, obtainable by slowly adding water to a mixture of the base components, comprising the oily phase, one or more of the O/W emulsifiers according to the invention and lecithin, if desired one or more W/O emulsifiers, and if desired further auxiliaries, additives and/or active compounds, such that an intermediate gel is formed which, on the addition of more water, leads to a microemulsion, (b) in which the droplets of the discontinuous oily phase are joined to one another by one or more crosslinking substances, the molecules of which are distinguished by at least one hydrophilic region, which has an extension which is suitable for bridging the distance between the microemulsion droplets, and by at least one hydrophobic region, which is capable of entering into a hydrophobic interaction with the microemulsion droplets.

The invention also provides low-viscosity microemulsions without a crosslinker component, as is specific above in each case under (a). They are used, for example, as precursors for the preparation of gels of high viscosity, which are obtained with the crosslinker, but can also be used as the corresponding gels in each case.

The preparation processes for microemulsions are known per se and described in the literature and can also be used for the novel microemulsions. In particular, as the person skilled in the art is aware, the defined mixing ratios are determined by ascertaining and adjusting the relative mixing ratios of water, oily phase and, in particular, the emulsifiers (the O/W, and if desired the W/O emulsifiers) until a clear microemulsion is obtained.

The invention also provides for the use of the novel crosslinkers for the preparation of microemulsion gels from the microemulsions.

The invention also provides for the use of the novel crosslinkers for the crosslinking or thickening of, in particular, low-viscosity microemulsions.

The invention also provides the novel crosslinkers, in particular those of the polymer type, as novel substances.

Utilization of the intermediate gel phase is advantageous particularly when the intention is to use heat-sensitive or oxidation-sensitive or otherwise generally sensitive active compounds (vitamin A alcohol, vitamin A derivatives, vitamin E and vitamin E derivatives, unsaturated fatty acids, antioxidants, light-protection filters etc.), since after these active compounds have been added, the only remaining steps are the dilution of the gel with water and optionally other additives to the microemulsion or, in the presence of the crosslinkers which can be added at any point, the thickening of the microemulsion to give the novel microemulsion gel.

Preferred lecithin and lecithin derivatives consist of phospholipids of natural, semisynthetic and synthetic origin. The phospholipids can be unsaturated, partially hydrogenated and hydrogenated for the novel process. For example, phospholipids which are provided with further coemulsifiers or oils ("Emulmetik" from Lucas Meyer; "Phosal", "Phospholipon", "Natipide" from Nattermann Phospholipid GmbH, "Lipoid" from Lipod KG) are also advantageous.

Hydrogenated phospholipids are advantageous, for example, when antioxidants are to be omitted. In addition, it is also possible to use sphingolipids such as sphingosine, ceramides, cerebrosides, sphingomyelin according to the invention. The content of lecithin or of derivatives is, for example, from 0.001 to 20% by weight, based on the total weight of the microemulsion.

For parenteral nutrition, these microemulsions based on lecithin or derivatives are highly suitable since the particle size is in the nanometer region and it is possible to carry out heat sterilization. In addition, these microemulsions or microemulsion gels which are based on lecithin or lecithin derivatives are particularly advantageous for sprayable preparations (spray gels, after-foaming shaving gels, aerosol sprays), since the phospholipids present have very good foam-stabilizing and skin-care properties.

It is equally advantageous here if the crosslinking substance, also called a thickener or linker or linker substance in the context of the present description, forms an independent gel network in which the microemulsion droplets are then held firmly by the hydrophobic interaction (so-called associated thickeners are then present), or if the network is held together by the crosslinking with the microemulsion droplets in the junctions of the network.

The crosslinking substances used according to the invention for example follow structural diagrams as follows:

(1)

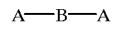
(2)

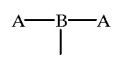
(3)

(4)

wherein B symbolizes a hydrophilic region of the particular crosslinker molecule and A in each case symbolizes hydrophobic regions, which can also be of different chemical nature within one molecule.

However, structural diagrams such as

A—B—A—B—A
(4)

-continued

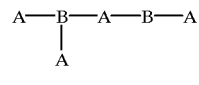
(5)

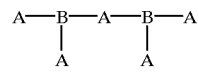
(6)

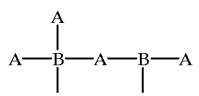
(7)

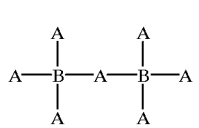
(8)

and analogously formed structures which are yet more complex also fall entirely within the context of the invention submitted here.

Structural diagrams as follows:

A—B—Z—B—A
(9)

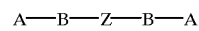
(10)

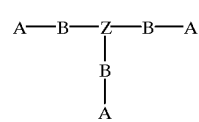
(11)

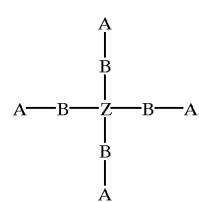
(12)

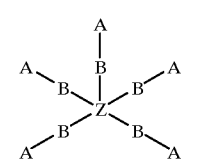
(13)

wherein Z here is a central unit, which can be hydrophilic or hydrophobic and as a rule consists of an oligo- or polyfunctional molecular radical, also fall within the context of the invention submitted here.

Thickeners with a higher degree of branching of course also fall within the context of the present invention.

For example, Z in diagram (10) can consist of a glyceryl radical, the three OH functions of which pass into the regions B, which in turn can be, for example, polyoxyethylene chains of equal or unequal length, and the terminal OH groups of which are esterified with a longer-chain fatty acid. Partial substitution on glycerol is also conceivable, as a result of which structures which correspond to diagram (9) can form.

The hydrophilic groups B can advantageously be chosen such that the crosslinker overall is water-soluble or at least dispersible in water, in which case the hydrophobic content of the groups A should then be over-compensated.

The following more specific structure diagrams can be followed, for example, for structure diagram (1):

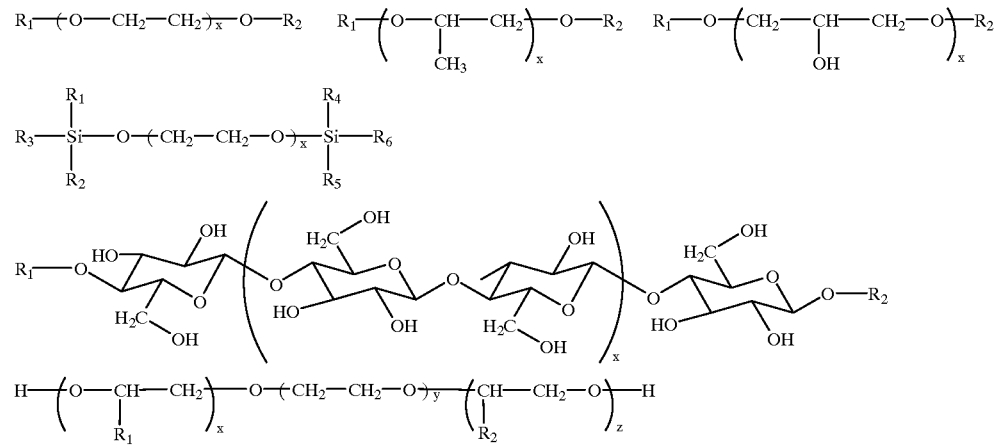

wherein $R_1$, $R_2$, $R_3$, $R_4$, $R_5$ and $R_6$ independently of one another can be branched or unbranched, saturated or unsaturated, cyclic or chain-like aliphatic or aromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. x, y and z here are numbers which enable the total molecule to be soluble or at least dispersible in water, and are typically chosen from the range greater than 10, advantageously from the range $20–10^7$. In the individual case, for example if the thickener is chosen from the group consisting of derivatized polysaccharides, x, y and z can also assume still considerably higher values. This is known per se to the expert and requires no further explanation.

For the structure diagram (2) for example, the following more specific structure diagrams can be followed:

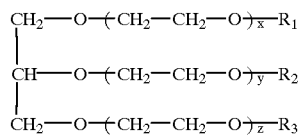

wherein $R_1$, $R_2$, and R3 independently of one another can be branched or unbranched, saturated or unsaturated, cyclic or chain-like aliphatic or aromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. x, y and z independently of one another here are numbers which enable the total molecule to be soluble or at least dispersible in water, and are typically chosen from the range greater than 10, advantageously from the range $20–10^7$.

Partial substitution is also conceivable here, it being possible for one or more of the indices x, y or z to assume the value zero and for one or more of the radicals $R_1$, $R_2$ or $R_3$ to be hydrogen atoms.

For structure diagram (3) for example, the following more specific structure diagrams can be followed:

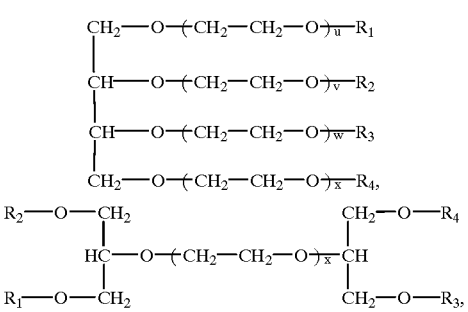

wherein $R_1$, $R_2$, $R_3$ and $R_4$ independently of one another can be branched or unbranched, saturated or unsaturated, cyclic or chain-like aliphatic or aromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. u, v, w and x here independently of one another are numbers which enable the total molecule to be soluble or at least dispersible in water, and are typically chosen from the range greater than 10, advantageously from the range $20–10^7$.

It also goes without saying here that partial substitution is conceivable, it being possible for one or more of the indices u, v, w and x to assume the value zero and for one or more of the radicals $R_1$, $R_2$, $R_3$ or $R_4$ to be hydrogen atoms. The substances here of course change into other structure diagrams.

For the structure diagram (9), for example, the following more specific structure diagrams can be followed:

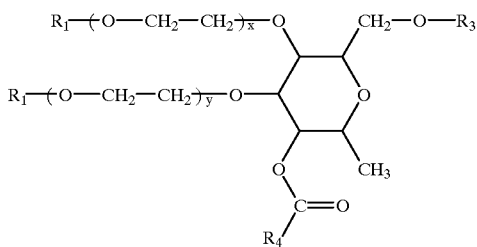

wherein $R_1$, $R_2$, $R_3$ and $R_4$ independently of one another can be branched or unbranched, saturated or unsaturated, cyclic or chain-like aliphatic or aromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. x and y here independently of one another are numbers which enable the total molecule to be soluble or at least dispersible in water, and are typically chosen from the range greater than 10, advantageously from the range $20-10^7$.

For the structure diagram (10), for example, the following more specific structure diagrams can be followed:

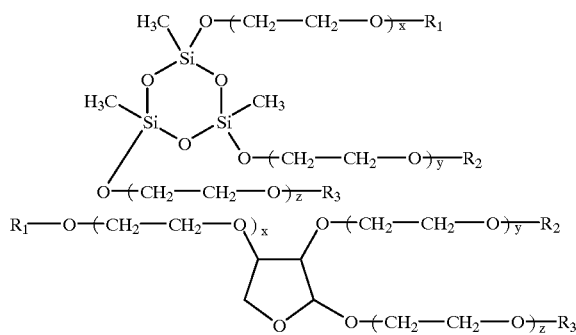

wherein $R_1$, $R_2$ and $R_3$ independently of one another can be branched or unbranched, saturated or unsaturated, cyclic or chain-like aliphatic or aromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. x, y and z here independently of one another are numbers which enable the total molecule to be soluble or at least dispersible in water, and are typically chosen from the range greater than 10, advantageously from the range $20-10^7$.

For the structure diagram (11) for example, the following more specific structure diagram can be followed:

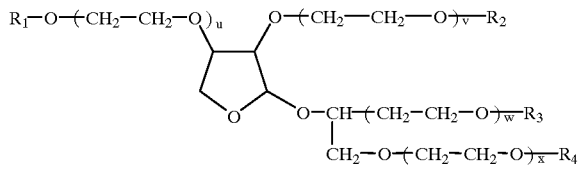

wherein $R_1$, $R_2$, $R_3$ and $R_4$ independently of one another can be branched or unbranched, saturated or unsaturated, cyclic or chain-like aliphatic or aromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. u, v, w and x here independently of one another are numbers which enable the total molecule to be soluble or at least dispersible in water, and are typically chosen from the range greater than 10, advantageously from the range $20-10^7$.

For the structure diagram (12), for example, the following more specific structure diagram can be followed:

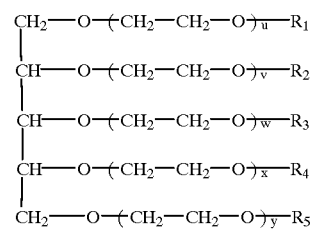

wherein $R_1$, $R_2$, $R_3$, $R_4$ and $R_5$ independently of one another can be branched or unbranched, saturated or unsaturated, cyclic or chain-like aliphatic or aromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. u, v, w, x and y here independently of one another are numbers which enable the total molecule to be soluble or at least dispersible in water, and are typically chosen from the range greater than 10, advantageously from the range $20-10^7$.

For the structure diagram (13), for example, the following more specific structure diagram can be followed:

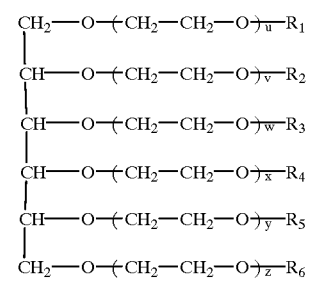

wherein $R_1$, $R_2$, $R_3$, $R_4$, $R_5$ and $R_6$ independently of one another can be branched or unbranched, saturated or unsaturated, cyclic or chain-like aliphatic or aromatic radicals, for example branched or unbranched or cyclic alkyl or alkanoyl radicals, aryl or aroyl radicals which are unsubstituted or substituted by alkyl or aryl substituents, or also alkylated or arylated organylsilyl radicals. u, v, w, x, y and z here independently of one another are numbers which enable the total molecule to be soluble or at least dispersible in water, and are typically chosen from the range greater than 10, advantageously from the range $20-10^7$.

It is also advantageous to choose thickeners chosen from the group of dendrimers.

Crosslinkers which have proven to be particularly suitable are those chosen from the group consisting of the polyethylene glycol ethers of the general formula R—O—(—CH$_2$—CH$_2$—O—)$_n$—R', wherein R and R' independently of one another are branched or unbranched alkyl or alkenyl radicals and n is a number greater than 100, the etherified fatty acid ethoxylates of the general formula R—COO—(—CH$_2$—CH$_2$—O—)$_n$—R', wherein R and R' independently of one another are branched or unbranched alkyl or alkenyl radicals and n is a number greater than 100, the esterified fatty acid ethoxylates of the general formula R—COO—(—CH$_2$—CH$_2$—O—)$_n$—C(O)—R', wherein R and R' independently of one another are branched or unbranched alkyl or alkenyl radicals and n is a number greater than 100, the polypropylene glycol ethers of the general formula R—O—(—CH$_2$—CH(CH$_3$)—O—)$_n$—R', wherein R and R' independently of one another are branched or unbranched alkyl or alkenyl radicals and n is a number greater than 100, the esterified fatty acid propoxylates of the general formula R—COO—(—CH$_2$—CH(CH$_3$)—O—)$_n$—C(O)—R', wherein R and R' independently of one another are branched or unbranched alkyl or alkenyl radicals and n is a number greater than 100, the polypropylene glycol ethers of the general formula R—O—X$_n$—Y$_m$—R', wherein R and R' independently of one another are branched or unbranched alkyl or alkenyl radicals, and wherein X and Y are not identical and are in each case either an oxyethylene group or an oxypropylene group and n and m independently of one another are numbers, the sum of which is greater than 100 and the etherified fatty acid propoxylates of the general formula R—COO—X$_n$—Y$_m$—R', wherein R and R' independently of one another are branched or unbranched alkyl or alkenyl radicals, and wherein X and Y are not identical and are in each case either an oxyethylene group or an oxypropylene group and n and m independently of one another are numbers, the sum of which is greater than 100, the hydrophobically modified water-soluble polymers of hydroxyethylcellulose, polyacrylates (of the Pemulen type), of polyvinylpyrrolidone, of polyvinylalcohol, of glucans, of pectin, of polylysine, of polyglutamates, of alginates, of dextran, of polymethacrylates, of copolymers of methacrylic acid glucosamide and cholesteryl methacrylate, of the copolymers of polyvinylpyrrolidone and cholesteryl methacrylate, of methacrylic acid glucosamides.

PEG-150 distearate and PEG-800 dioleate are particularly advantageous. PEG-300 pentaerythrityl tetraisostearate, PEG-800 diretinate, PEG-800 diglycyrrhetinyl stearate and PEG-800 ditocopherolate, PEG-800 distearate as well.

Very particularly advantageous linker substances have proven to be the following hydrophobically modified polymers: cetylhydroxyethylcellulose, stearylhydroxyethylcellulose, oleylhydroxyethylcellulose, cholesteryl polyacrylate, dodecyl amidopolyacrylate, C10–C30-alkyl acrylate (Pemulens), stearyl polyacrylate, cholesteryldextran, cholesteryl methacrylate, methacrylic acid glucosamide, copolymer of polyvinylpyrrolidone and cholesteryl methacrylate, stearyl polyvinyl alcohol, copolymer of methacrylamide and cholesteryl methacrylate.

It can, however, be observed that in the case of very dilute microemulsibns, which are characterized by a relatively large average distance between the oil droplets, crosslinking of the dispersed phase is possible if polymers with relatively long hydrophilic groups (e.g. relatively long polyethylene oxide chains) are given preference. PEG-800 distearate has therefore advantageously also been used.

In addition, it is possible to insert, onto the ends of the polymer or within the polymer, groups which are a constituent of skin grease, such as cholesterol. Endogenous esterases or pH changes enable these polymers to cleave the cholesterol and hydrophilic block following application, resulting, for example, in a skincare or skin-moisturizing action. It is obvious to the person skilled in the art that other groups, such as, for example, UV filters (water-soluble, oil-soluble), antioxidants, antiacne active compounds, i.e. generally known active compounds from the fields of cosmetics, dermatology and pharmacy, can also be covalently bonded to water-soluble polymers and as such or following cleavage of the group bonded to the water-soluble polymer, exhibit the intended physiological action.

In the case of internal or external wounds, the crosslinkers can, following application, additionally adopt an immobilizing or contact-establishing function (e.g. haemostatic) as a result of physical crosslinking of the constituents of cells, body fluids, or body constituents (blood, hair etc.). The novel crosslinkers thus permit the dispensation of a wound dressing, plasters, suture materials etc. Polymers based on polyethylene glycol are particularly advantageous for internal applications and for contact with blood since they are biocompatible, and do not cause an immune response or inflammation. The attachment of cells and proteins (fibrinogen, immunoglobulin, leukocytes etc.) is prevented by the hydrophilicity, [lacuna] rapid changes in the confirmation of the PEG block. The novel modification of polyethylene glycol is advantageous in particular for hydrophobic groups from endogenous substances such as, for example, cholesterol, or also bioactive substances which release, for example, an antibiotic or a wound-healing-promoting group (prodrug principle). Enzymatic degradation of the polymers results in defined toxicologically acceptable products, or the release of bioactive active compounds. The crosslinkers thus satisfy at least two objectives since, on the one hand, they convert a low-viscosity microemulsion (which can also be free from emulsifiers) into a gel-like presentation, and secondly, following application, adopt an immobilizing function of cells, body fluids (blood) or body constituents. For example, in the case of wounds or in the case of internal applications, biocompatible emulsifiers such as lecithin or lecithin derivatives are advantageously used with novel crosslinkers.

The novel crosslinkers having a haemostatic function can be incorporated into face lotions, shaving lotions, preshave products, aftershave lotions based on a PIT emulsion or a lotion or cream containing EO-free emulsifiers, shaving oils, foaming and nonfoaming shaving gels, shaving soaps, shaving foams, after-foaming shaving gels based on microemulsions, novel microemulsions, novel microemulsion gels, shaving gels based on polyacrylates, hydrogels and depilatories. Moreover, the crosslinkers or also a presentation for these crosslinkers can be incorporated into appliances for razor blades.

Advantageous linker substances are, for example, chosen from the group having the following structural formulae:

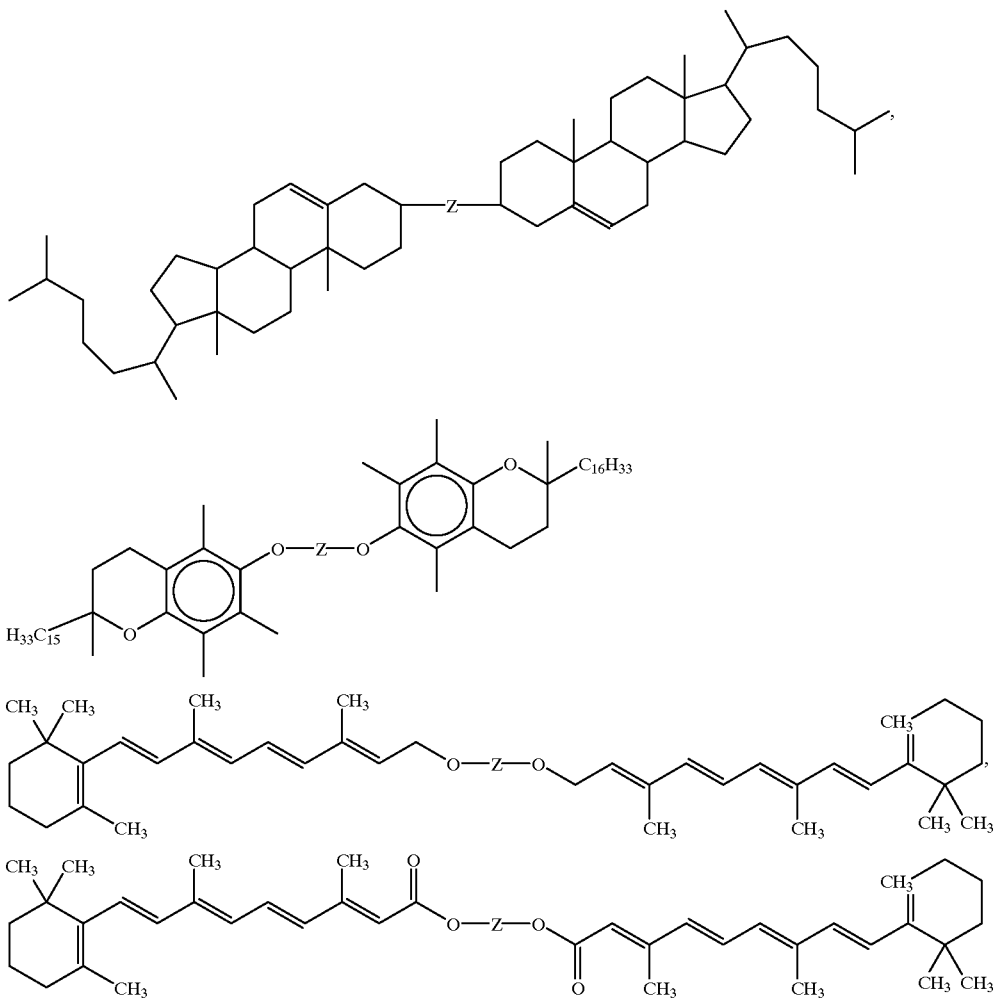
and related substances. Z is a hydrophilic region, which can be chosen particularly advantageously from the group of polyoxyethylene groups having degrees of polyethoxylation of up to $10^7$.
Particularly advantageous linker substances have proven to be dicholesteryl compounds of the type
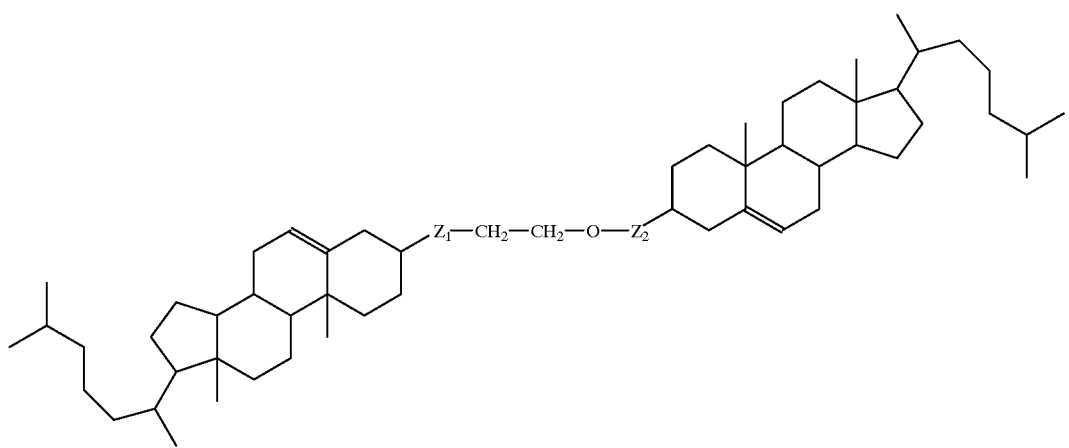

where $Z_1$ and $Z_2$ independently of one another can be chosen from the group consisting of a single bond, ester group, carbonate group, oxygen, acid amide group, acid imide group, thiocarboxylate group, urethane or carbamate group.

Very particularly advantageous linker substances have proven to be dicholesteryl compounds of the type

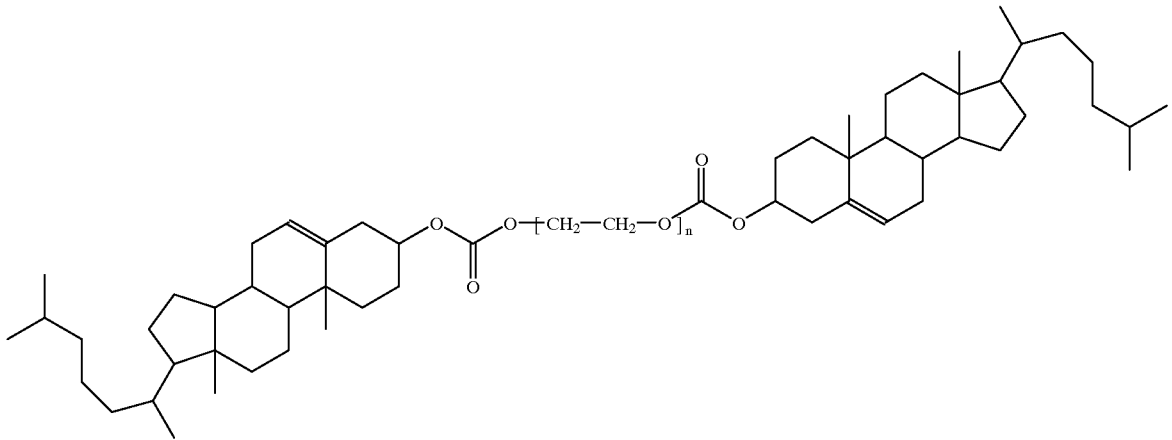

which we collectively wish to name PEG-n-chol$_2$, where n is a number which enables the total molecule to be soluble or at least dispersible in water, and is typically chosen from the range greater than 10, advantageously from the range 20 to $10^7$, very particularly advantageously from the range 120 to 800.

PEG-n-chol$_2$ is obtainable by customary chemical processes. In particular, PEG-n-chol$_2$ can be obtained advantageously by reacting polyethylene oxide having the desired degree of polymerization n with a cholesteryl derivative of the general structure.

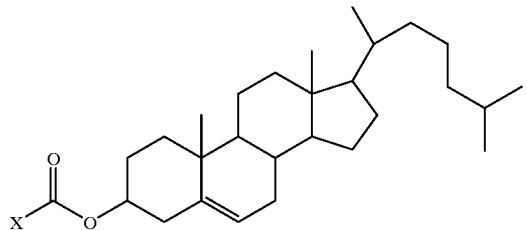

it being advantageous to provide reaction conditions which favour cleavage of the compound HX, for example according to the following reaction equation:

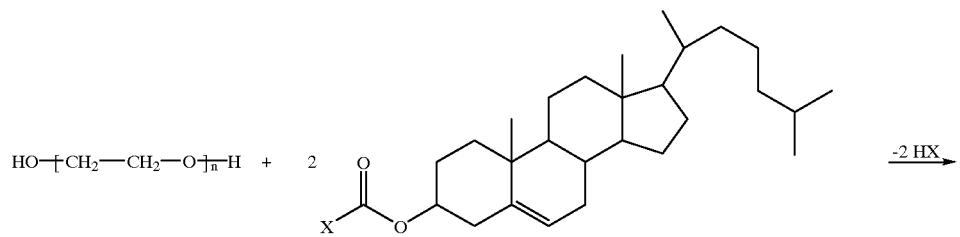

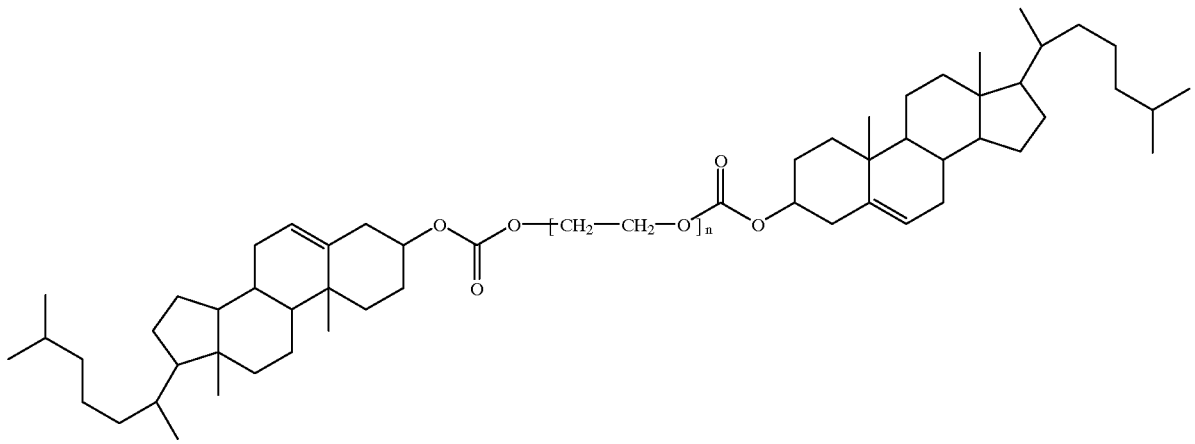

It is, however, also advantageous, particularly when the thickener(s) is/are to be chosen from the group of associative thickeners, to choose hydrophobically substituted polysaccharide derivatives, for example hydrophobically substituted cellulose ethers, hydrophobically substituted starches, alginates, glucans, chitins and the like.

The hydrophobically substituted saccharide derivatives described in U.S. Pat. No. 5,426,182 are particularly advantageous.

Cetylhydroxyethylcellulose can, for example, advantageously be used.

The novel microemulsion is advantageously prepared in practice by, after choosing suitable raw materials, i.e. aqueous and oily phase, mixing one or more O/W emulsifiers, which are free from ethylene oxide and propylene oxide and are used according to the invention, in a defined mixing ratio to one another, and optionally further substances, heating said mixture, and then, with continued stirring, cooling the mixture at room temperature.

To prepare the microemulsion gels, for example one or more of the thickeners used according to the invention are added at any point in the above preparation.

However, it is particularly advantageous to firstly prepare the low-viscosity microemulsions and then add the crosslinker thereto, which then brings about gel formation.

A novel microemulsion based on lecithin or the previously described lecithin derivatives is advantageously prepared in practice by mixing one or more O/W emulsifiers, which are free from ethylene oxide and propylene oxide and are used according to the invention, lecithin and one or more oily phases in a defined mixing ratio, and optionally further substances, slowly adding water to said mixture to form a gel which, when further water is added and optionally other substances are added, leads to the novel microemulsions.

To prepare the microemulsion gels, one or more of the thickeners used according to the invention are added at any point in the above preparation.

For the purpose of the present invention, particularly advantageous microemulsion gels are those (a) based on microemulsions of the oil-in-water type, which comprise
  a discontinuous oily phase and a continuous aqueous phase
  comprising at least one O/W emulsifier which is/are free from ethylene oxide and propylene oxide
    where the latter is chosen from the group consisting of acyl lactylates, glutamates, sarcosinates, isethionates, sulphosuccinates, alaninates, amphoacetates, polyglycerol esters, alkylglycosides, alkylpolyglycosides, sorbitan esters, methylglucose esters, esters of hydroxy acids, and polyglycerol methylglucose esters, (b) in which the droplets of the discontinuous oily phase are joined to one another by one or more crosslinking substances, the molecules of which are distinguished by at least one hydrophilic region, which has an extension which is suitable for bridging the distance between the microemulsion droplets, and by at least one hydrophobic range, which is capable of entering into a hydrophobic interaction with the microemulsion droplets.

The amount of novel thickeners should preferably be in the range from 0.3 to 30% by weight, in particular from 1 to 10% by weight, in each case based on the total weight of the microemulsion gel;

FIG. 1 illustrates the principle according to the invention: the microemulsion droplets of an O/W microemulsion, which are shown as shaded circles, are joined to one another by the crosslinker molecules shown as lines, which carry hydrophobic radicals, symbolized by rectangles, at both ends. It can be seen that, in principle, an emulsion droplet can also accommodate several hydrophobic radicals, as a result of which a higher degree of crosslinking and three-dimensionality of the network can be ensured.

A second novel possibility for forming microemulsion gels comprises immobilizing the oil droplets by the use of hydrophobically modified, synthetic or naturally occurring water-soluble/-dispersible polymers. Such polymers are also referred to as associative thickeners.

FIG. 2 illustrates this principle. The gel structure swollen by a water content which is not shown in FIG. 2 is essentially made up of the crosslinker molecules, shown by branched lines, which carry hydrophobic radicals, symbolized by rectangles, at the ends of the branches. The hydrophobic radicals attach to one another as a result of hydrophobic interaction, as a result of which crosslinking is effected. Microemulsion droplets can likewise attach to the crosslinking points by hydrophobic interaction. It is certainly in principle irrelevant in this case whether the hydrophobic radicals are "immersed in" or whether the hydrophobic radicals merely come into contact with the microemulsion droplets on the surface, and stick more or less only onto this.

It is particularly advantageous when the O/W emulsifier(s) which are free from ethylene oxide and propylene oxide is or are chosen from the group of Acyl lactylates of the formula R—C(O)O—CH(CH$_3$)—C(O)O—CH(CH$_3$)CO$_2$⁻M⁺, where R is a saturated and/or unsaturated, branched and/or unbranched fatty acid having from 6 to 26 carbon atoms.

Acyl glutamates of the formula R—C(O)NHCH(COO⁻, M⁺)CH$_2$CH$_2$COO⁻M⁺, where R is a saturated and/or unsaturated, branched and/or unbranched fatty acid having from 6 to 26 carbon atoms.

Acyl sarcosinates of the formula R—C(O)—N(CH$_3$)CH$_2$COO⁻M⁺, where R is a saturated and/or unsaturated, branched and/or unbranched fatty acid having from 6 to 26 carbon atoms.

Isethionates of the formula RC(O)—O—CH$_2$CH$_2$—SO$_3$⁻M⁺, where R is a saturated and/or unsaturated, branched and/or unbranched fatty acid having from 6 to 26 carbon atoms.

Sulphosuccinates of the formula M⁺, ⁻O—C(O)—CH$_2$—CH(SO$_3$—M+)—C(O)—O—R, where R is a saturated and/or unsaturated, branched and/or unbranched fatty acid having from 6 to 26 carbon atoms.

Alaninates of the formula CH$_3$CH$_2$N(CH$_3$)(C$_{12}$H$_{25}$)C(O)O⁻M⁺

Amphoacetates of the formula R—C(O)—NH—CH$_2$CH$_2$—N(CH$_2$CH$_2$OH)—CH$_2$COO⁻; M⁺

Polyglycerol esters, alkyl glycosides, alkyl polyglycosides, sorbitan esters, sucrose esters, preferably sucrose laurate, in particular sucrose monolaurate (e.g. Sisterna L70-C), methylglucose esters, esters of hydroxy acids and polyglycerol methylglucose esters.

It is of particular advantage to use sodium lauroyl lactylate and sodium caproyl lactylate as acryl lactylate.

In addition, sodium lauroyl glutamate and sodium cocoyl glutamate have proven successful as the glutamate.

Sodium lauroyl sarcosinate can also be used advantageously.

The isethionate is particularly advantageously sodium lauroyl isethionate. Disodium lauryl sulphosuccinate has also proven suitable.

The suitable alaninate has proven to be N-methyl-N-lauroyl alaninate.

The highly suitable amphoacetate was sodium lauroamphoacetate.

The suitable polyglycerol esters were polyglycerol ester laurate, polyglycerol-10 monooleate, polyglycerol-10 monoisostearate, polyglycerol-10 monostearate. A suitable alkyl polyglycoside was lauryl glycoside. It is also favourable to use sorbitan stearate as the sorbitan ester. Suitable esters of hydroxy acids have proven to be C12–13-alkyl maleates and C12–13 tartrates.

Optional, but advantageous W/O emulsifiers according to the invention which can be used are: fatty alcohols having from 8 to 30 carbon atoms, monoglycerol esters of saturated and/or unsaturated, branched and/or unbranched alkane carboxylic acids having a chain length of from 8 to 24 carbon atoms, in particular 12–18 carbon atoms, diglycerol esters of saturated and/or unsaturated, branched and/or unbranched alkane carboxylic acids having a chain length of from 8 to 24 carbon atoms, in particular 12–18 carbon atoms, monoglycerol ethers of saturated and/or unsaturated, branched and/or unbranched alcohols having a chain length of from 8 to 24 carbon atoms, in particular 12–18 carbon atoms, diglycerol ethers of saturated and/or unsaturated, branched and/or unbranched alcohols having a chain length of from 8 to 24 carbon atoms, in particular 12–18 carbon atoms, propylene glycol esters of saturated and/or unsaturated, branched and/or unbranched alkane carboxylic acids having a chain length of from 8 to 24 carbon atoms, in particular 12–18 carbon atoms, and sorbitan esters of saturated and/or unsaturated, branched and/or unbranched alkane carboxylic acids having a chain length of from 8 to 24 carbon atoms, in particular 12–18 carbon atoms, methylglucose esters of saturated and/or unsaturated, branched and/or unbranched alkane carboxylic acids having a chain length of from 8 to 24 carbon atoms, in particular 12–18 carbon atoms. Suitable lecithin derivatives are, for example, hydrogenated, partially hydrogenated and nonhydrogenated phospholipids, phosphatidylcholine, phosphatidylethanolamine, phosphatidylserine, cardiolipine (diphosphatidylglycerol) and sphingomyelin, ceramides.

Particularly advantageous W/O emulsifiers are glycerol oleate, glyceryl monostearate, glyceryl monoisostearate, diglyceryl monostearate, diglyceryl monoisostearate, diglycerol diisostearate, polyglycerol-3 diisostearate, sodium isostearyl lactylate, propylene glycol monostearate, sorbitan monoisostearate, cetyl alcohol, arachidyl alcohol, selachyl alcohol, chimyl alcohol, glyceryl monolaurate, glyceryl monocaprate, glyceryl monocaprylate, hydrogenated and nonhydrogenated lecithin, methylglucose isostearate, 2-ethylhexyl glycerol ether, methylglucose distearate, lauryl glycol, lauryl lactate.

Commercially available nanoemulsions or microemulsions, for example from Kuhs or Nattermann ("Probiol"), Gattefossé, Rovi, Vesifact AG, are also used advantageously and can, if desired, be charged with active compounds, e.g. skin moisturizers, vitamin C, SOD, UV filters, plasmid DNA, epidermal growth factors (EGF, FGF, PDGF), glycosylrutin, Q10, cyclip AMP, tyrosine, amphotericin B, daunorubicin, ibuprofen, doxorubicin, cyclosporin, T4 endonuclease, and the like, but also give, as uncharged nanoemulsions or microemulsions, gels according to the invention. The person skilled in the art is aware that other companies offer charged or uncharged nanoemulsions or microemulsions which, according to the process proposed here, give gels according to the invention. Thus, for example, high-pressure homogenization gives emulsifier-free or low-emulsifier nanoemulsions and microemulsions. The principle of crosslinking according to the invention also leads here to gel-like preparations.

In addition, it is known that in the case of liposome preparations with a high oil content, nanoemulsions can be obtained, or liposomes and nanoemulsions can also exist alongside one another. The principle of crosslinking according to the invention also leads here to gels, since anchorage of the hydrophobic ends of the water-soluble polymer can then take place in the bilayer membranes of the vesicle and in the microemulsion droplets.

It is also possible according to the invention to keep the total content of emulsifiers at less than 15% by weight, based on the total weight of the microemulsion according to the invention. It is preferable to keep the total content of emulsifiers at less than 10% by weight, in particular less than 8% by weight, based on the total weight. In particular, the total content of emulsifiers can be, for example, from 0.1 to 20% by weight, based on the total weight of the microemulsion.

The oily phase of the microemulsion gels according to the invention is advantageously chosen from the group consisting of esters of saturated and/or unsaturated, branched and/or unbranched alkanecarboxylic acids having a chain length of 3 to 30 carbon atoms and saturated and/or unsaturated, branched and/or unbranched alcohols having a chain length of 3 to 30 carbon atoms, and from the group consisting of esters of aromatic carboxylic acids and saturated and/or unsaturated, branched and/or unbranched alcohols having a chain length of 3 to 30 carbon atoms. Such ester oils can then advantageously be chosen from the group consisting of isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and naturally occurring mixtures of such esters, for example jojoba oil.

The oily phase can furthermore advantageously be chosen from the group consisting of branched and unbranched hydrocarbons and hydrocarbon waxes, silicone oils, dialkyl ethers and from the group consisting of saturated or unsaturated, branched or unbranched alcohols, as well as fatty acid triglycerides, that is to say the triglycerol esters of saturated and/or unsaturated, branched and/or unbranched alkanecarboxylic acids having a chain length of 8 to 24, in particular 12–18 carbon atoms. The fatty acid triglycerides can advantageously be chosen, for example, from the group consisting of synthetic, semi-synthetic and naturally occurring oils, for example olive oil, sunflower oil, soya oil, groundnut oil, rape oil, almond oil, palm oil, coconut oil, palm kernel oil and so on.

Any desired mixtures of such oil and wax components can also advantageously be employed in the context of the present invention.

If appropriate, it may also be advantageous to employ waxes, for example cetyl palmitate, as the sole lipid component of the oily phase. In such cases, the O/W microemulsions according to the invention can also be obtained, where appropriate, as microdispersions of solid wax particles.

The oily phase is advantageously chosen from the group consisting of 2-ethylhexyl isostearate, octyldodecanol, isotridecyl isononanoate, isoeicosan, 2-ethyl-hexyl cocoate, $C_{12-15}$-alkyl benzoate, capryl/capric acid triglyceride and dicaprylyl ether.

Of the hydrocarbons, paraffin oil, squalane and squalene are advantageously to be used in the context of the present invention.

The oily phase can furthermore advantageously have a content of cyclic or linear silicone oils or consist entirely of such oils, but it is preferable to use an additional content of other oily phase components, in addition to the silicone oil or the silicone oils.

Cyclomethicone (octamethylcyclotetrasiloxane) is advantageously employed as a silicone oil to be used according to the invention. However, other silicone oils can also advantageously be used in the context of the present invention, for example hexamethylcyclotrisiloxane, polydimethylsiloxane and poly(methylphenylsiloxane).

The content of the oily phase can, for example, be from 0.01 to 30% by weight, based on the total weight of the microemulsions.

The content of the aqueous phase can vary greatly and is, for example, from 1 to 99% by weight.

The content of the O/W emulsifiers can, for example, be from 0.01 to 20% by weight, based on the total weight of the microemulsion.

If desired, the content of the W/O emulsifiers can, for example, be from 0.01 to 15% by weight, based on the total weight of the microemulsion.

According to the invention, advantageous O/W microemulsions and microemulsion gels can be obtained, the proportion of the O/W emulsifier for example being less than 20% by weight, in particular for example less than 15% by weight, based on the total weight of the microemulsion, and for example less than 15%, in particular less than 5% by weight of an additional W/O emulsifier being present, it being possible for the thickener or thickeners used according to the invention to be added at any point in time of the preparation.

In the individual case, it is possible here that the concentrations are slightly above or below the abovementioned limits, and nevertheless the emulsion types in question are obtained. In view of the widely scattered diversity of suitable emulsifiers and oil constituents, this is not unexpected to the expert, so that he knows that exceeding or falling below such limits does not depart from the basis of the present invention.

The microemulsion gels according to the invention advantageously comprise electrolytes, in particular one or more salts with the following anions: chlorides, and furthermore inorganic oxo-element anions, and of these in particular sulphates, carbonates, phosphates, borates and aluminates. Electrolytes based on organic anions can also advantageously be used, for example lactates, acetates, benzoates, propionates, tartrates, citrates and many others. Comparable effects can also be achieved by ethylenediaminetetraacetic acid and salts thereof.

Cations of the salts which are preferably used are ammonium, alkylammonium, alkali metal, alkaline earth metal, magnesium, iron and zinc ions. It does not need mentioning that in cosmetics, only physiologically acceptable electrolytes should be used. Special medical uses of the microemulsions according to the invention, on the other hand, can at least in principle necessitate the use of electrolytes which should not be used without medical supervision.

Potassium chloride, sodium chloride, magnesium sulphate, zinc sulphate and mixtures thereof are particularly preferred. Salt mixtures such as occur in natural salt from the Dead Sea are also advantageous.

The concentration of the electrolyte or electrolytes should be about 0.1–10.0% by weight, particularly advantageously about 0.3–8.0% by weight, based on the total weight of the preparation.

The microemulsion gels according to the invention furthermore outstandingly help to smooth the skin, especially if they are provided with one or more substances which promote smoothing of the skin.

If the microemulsion gels according to the invention are bases for cosmetic deodorants/antiperspirants, all the customary active compounds can advantageously be used, for example odour maskers, such as the customary perfume constituents, odour absorbers, for example the laminar silicates described in the laid-open Specification DE-P 40 09 347, and of these in particular montmorillonite, kaolinite, ilite, beidellite, nontronite, saponite, hectorite, bentonite and smectite, and furthermore, for example, zinc salts of ricinoleic acid. Germ-inhibiting agents are also capable of being incorporated into the microemulsions according to the invention. Advantageous substances are, for example, 2,4,4'-trichloro-2'-hydroxydiphenyl ether (Irgasan), 1,6-di-(4-chlorophenylbiguanido)hexane (chlorhexidine), 3,4,4'-trichlorocarbanilide, quaternary ammonium compounds, oil of cloves, mint oil, oil of thyme, triethyl citrate, famesol (3,7,11-trimethyl-2,6,10-dodecatrien-1-ol) and the active agents described in the Patent laid-open Specifications DE-37 40 186, DE-39 38 140, DE-42 04 321, DE-42 29 707, DE-42 29 737, DE-42 37 081, DE-43 09 372 and DE-43 24 219.

The customary antiperspirant active compounds can also advantageously be used in the microemulsion gels according to the invention, in particular astringents, for example basic aluminium chlorides.

The cosmetic deodorants according to the invention can be in the form of aerosols, that is to say preparations which can be sprayed from aerosol containers, squeeze bottles or by a pump device, or in the form of liquid compositions which can be applied by means of roll-on devices, but also in the form of microemulsion gels which can be applied from normal bottles and containers.

Suitable propellants for cosmetic deodorants according to the invention which can be sprayed from aerosol containers are the customary known readily volatile, liquefied propellants, for example hydrocarbons (propane, butane or isobutane), which can be employed by themselves or as a mixture with one another. Compressed air can also advantageously be used.

The expert is of course aware that there are propellant gases which are non-toxic per se and would be suitable in principle for the present invention, but which should nevertheless be omitted because of an unacceptable impact on the environment or other concomitant circumstances, in particular chlorofluorohydrocarbons (CFCs).

It has furthermore been found, surprisingly, that if propellants which are soluble in the oily phase, that is to say, for example, customary propane/butane mixtures, are used, the O/W microemulsion gels according to the invention are not only sprayed as aerosol droplets, but develop into fine-bubbled, rich foams as soon as such systems loaded with such propellants experience a release of pressure.

Such after-foaming preparations are therefore also to be regarded as advantageous embodiments of the present invention with an independent inventive step.

If propellants which are insoluble in the oily phase are used, the O/W microemulsion gels according to the invention are sprayed as aerosol droplets.

Those cosmetic and dermatological preparations which are in the form of a sunscreen composition are also favourable. These advantageously additionally comprise, in addition to the active compound combinations according to the invention, at least one UVA filter substance and/or at least one UVB filter substance and/or at least one inorganic pigment.

However, it is also advantageous in the context of the present invention to provide those cosmetic and dermatological preparations of which the main purpose is not protection from sunlight but which nevertheless comprise a content of UV protection substances. Thus, for example, UV-A or UV-B filter substances are usually incorporated into day creams.

Preparations according to the invention can advantageously comprise substances which absorb UV radiation in the UVB range, the total amount of the filter substances being, for example, 0.1% by weight to 30% by weight, preferably 0.5 to 10% by weight, in particular 1 to 6% by weight, based on the total weight of the preparations.

The UVB filters can be oil-soluble or water-soluble. Examples of oil-soluble substances which may be mentioned are, for example:

3-benzylidenecamphor and derivatives thereof, for example 3-(4-methylbenzylidene)camphor;

4-aminobenzoic acid derivatives, preferably 2-ethylhexyl 4-(dimethylamino)-benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxy-benzalmalonate; and 2,4,6-trianilino-(p-carbo-2'-ethyl-1'-hexyloxy)-1,3,5-triazine.

Advantageous water-soluble substances are:

2-phenylbenzimidazole-5-sulphonic acid and salts thereof, for example sodium, potassium or triethanolammonium salts, sulphonic acid derivatives of benzophenones, preferably 2-hydroxy-4-methoxybenzophenone-5-sulphonic acid and its salts;

sulphonic acid derivatives of 3-benzylidenecamphor, such as, for example, 4-(2-oxo-3-bornylidenemethyl) benzenesulphonic acid, 2-methyl-5-(2-oxo-3-bornylidenemethyl)benzenesulphonic acid and their salts.

The list of UVB filters mentioned, which can be used according to the invention, is of course not intended to be limiting.

The invention also relates to the combination of a UVA filter according to the invention with a UVB filter, and a cosmetic or dermatological preparation according to the invention which also comprises a UVB filter.

It may also be advantageous to employ UVA filters which are usually contained in cosmetic and/or dermatological preparations in preparations according to the invention. Such substances are preferably derivatives of dibenzoylmethane, in particular 1-(4'-tert-butylphenyl)-3-(4'-methoxyphenyl)propane-1,3-dione and 1-phenyl-3-(4'-isopropylphenyl)-propane-1,3-dione. The invention also relates to preparations which comprise these combinations. The same amounts of UVA filter substances as have been mentioned for UVB filter substances can be used.

Cosmetic and/or dermatological preparations according to the invention can also comprise inorganic pigments which are usually used in cosmetics for protecting the skin from UV rays. These are oxides of titanium, zinc, iron, zirconium, silicon, manganese, aluminium and cerium and mixtures thereof, as well as modifications in which the oxides are the active agents. The pigments are particularly preferably those based on titanium dioxide. The amounts mentioned for the above combinations can be used.

An astonishing property of the present invention is that preparations according to the invention are very good vehicles for cosmetic or dermatological active compounds in the skin, advantageous active compounds being antioxidants which can protect the skin from oxidative stress.

According to the invention, the preparations advantageously comprise one or more antioxidants. Favourable antioxidants, which are nevertheless to be used optionally, are all the antioxidafits which are suitable or customary for cosmetic and/or dermatological applications. It is advantageous here to use antioxidants as the sole class of active compound, for example if a cosmetic or dermatological use such as combating oxidative stress of the skin is a priority. However, it is also favourable to provide the microemulsion gels according to the invention with a content of one or more antioxidants if the preparations are to serve another purpose, for example as deodorants or sunscreen compositions.

The antioxidants are particularly advantageously chosen from the group consisting of amino acids (for example histidine, tyrosine and tryptophan) and derivatives thereof, imidazoles (for example urocanic acid) and derivatives thereof, peptides, such as D,L-carnosine, D-carnosine, L-carnosine and derivatives thereof (for example anserine), carotenoids, carotenes (for example α-carotene, β-carotene and lycopene) and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, gamma-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximine, buthionine-sulphones and penta-, hexa- and heptathionine-sulphoximine) in very low tolerated dosages (for example pmol to µmol/kg), and furthermore (metal) chelators (for example α-hydroxy-fatty acids, α-hydroxypalmitic acid, phytic acid and lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example gamma-linolenic acid, linoleic acid and oleic acid), folic acid and derivatives thereof, ubiquinone and ubiquinol and derivatives thereof, vitamin C and derivatives (for example ascorbyl palmitates, Mg ascorbyl phosphates and ascorbyl acetates), tocopherols and derivatives (for example vitamin E acetate), vitamin A and derivatives (vitamin A palmitate) and coniferyl benzoate of benzoin resin, rutic acid and derivatives thereof, ferulic acid and derivatives thereof, butylhydroxytoluene, butylhydroxyanisole, nordihydroguaiac resin acid, nordihydroguaiaretic acid, trihydroxybutyrophenone, uric acid and derivatives thereof, zinc and derivatives thereof (for example ZnO and $ZnSO_4$), selenium and derivatives thereof (for example selenium-methionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

Oil-soluble antioxidants can particularly advantageously be employed in the context of the present invention.

The amount of antioxidants (one or more compounds) in the preparations is preferably 0.001 to 30% by weight, particularly preferably 0.05–20% by weight, in particular 1–10% by weight, based on the total weight of the preparation.

If vitamin E and/or derivatives thereof are the antioxidant or antioxidants, it is advantageous to choose the particular concentrations thereof from the range of 0.001–10% by weight, based on the total weight of the formulation.

If vitamin A or vitamin A derivatives or carotenes or derivatives thereof are the antioxidant or antioxidants, it is advantageous to choose the particular concentrations thereof from the range of 0.001–10% by weight, based on the total weight of the formulation.

The person skilled in the art is of course aware that high-quality cosmetic preparations are usually inconceivable without the customary auxiliaries and additives. These include, for example, agents which impart consistency, fillers, perfume, dyestuffs, emulsifiers, additional active compounds, such as vitamins or proteins, light protection agents, stabilizers, insect repellents, alcohol, water, salts and substances having an antimicrobial, proteolytic or keratolytic action. The amount by weight of auxiliaries or additives can, for example, be from 0.001 to 20% by weight, based on the total weight of the microemulsion.

According to the invention, the active compounds can also very advantageously be chosen from the group consisting of lipophilic active compounds, in particular from the following group:

acetylsalicylic acid, atropine, azulene, hydrocortisone and derivatives thereof, for example hydrocortisone 17-valerate, vitamins, for example ascorbic acid and derivatives thereof, vitamins of the B and D series, very favourably vitamin $B_1$, vitamin $B_{12}$ and vitamin $D_1$, but also bisabolol, unsaturated fatty acids, that is to say the essential fatty acids (often also called vitamin F), in particular γ-linolenic acid, oleic acid, eicosapentaenoic acid, docosahexaenoic acid and derivatives thereof, chloramphenicol, caffeine, prostaglandins, thymol, camphor, extracts or other products of plant and animal origin, for example oil of evening primrose oil, borage oil or current kernel oil, fish oils and cod-liver oil, and also ceramides and ceramide-like compounds and so on.

Although the use of hydrophilic active compounds is of course also favoured according to the invention, it is another advantage of the microemulsion gels according to the invention that the high number of very finely divided droplets renders precisely oil-soluble or lipophilic active compounds with a particularly high activity biologically available.

It is also advantageous to choose the active compounds from the group of re-fatting substances, for example Purcellin oil, Eucerit® and Neocerit®. The amount by weight of the active compounds can be, for example, 0.001 to 20% by weight, based on the total weight of the microemulsion.

It is also possible, and may be advantageous, to add wash-active surfactants to the preparations according to the invention. Aqueous cosmetic cleansing agents according to the invention or low-water or anhydrous cleansing agent concentrates intended for aqueous cleansing can comprise cationic, anionic, nonionic and/or amphoteric surfactants, for example conventional soaps, for example fatty acid salts of sodium, alkyl sulphates, alkyl ether sulphates, alkane- and alkylbenzenesulphonates, sulphoacetates, sulphobetaines, sarcosinates, amidosulphobetaines, sulphosuccinates, sulphosuccinic acid half-esters, alkyl ether-carboxylates, protein-fatty acid condensates, alkylbetaines and amidobetaines, fatty acid alkanolamides and polyglycol ether derivatives.

Cosmetic preparations which are cosmetic cleansing preparations for the skin can be present in liquid or solid form. They preferably comprise at least one anionic, nonionic or amphoteric surface-active substance or mixtures thereof, at least one electrolyte according to the invention and auxiliaries such as are usually used for this purpose. The surface-active substance can preferably be present in the cleansing preparations in a concentration of between 1 and 50% by weight, based on the total weight of the preparations.

Cosmetic preparations which are a shampooing agent preferably comprise at least one anionic, nonionic or amphoteric surface-active substance or mixtures thereof, if appropriate electrolytes and auxiliaries such as are usually used for this purpose. The surface-active substance can preferably be present in the cleansing preparations in a concentration of between 1 and 50% by weight, based on the total weight of the preparations. Cetyltrimethylammonium salts, for example, are advantageously to be used.

The compositions according to the invention intended for cleansing the hair or the skin comprise, in addition to the abovementioned surfactants, water and, if appropriate, the additives customary in cosmetics, for example perfume, thickeners, dyestuffs, deodorants, antimicrobial substances, re-fatting agents, complexing and sequestering agents, pearlescent agents, plant extracts, vitamins, active compounds and the like.

In spite of their oil content, the preparations according to the invention surprisingly have a very good foam development and high cleansing power, and have a highly regenerating action in respect of the general state of the skin. In particular, the preparations according to the invention have the effect of smoothing the skin, reduce the dryness sensation of the skin and make the skin supple.

If the microemulsion gels according to the invention are to be employed for hair care, they can comprise the customary constituents, usually, for example, film-forming polymers. Suitable such polymers having at least partly quaternized nitrogen groups (called "film-forming agents" below) are preferably those which are chosen from the group consisting of substances which, according to INCI nomenclature (International Nomenclature of Cosmetic Ingredients) carry the name "polyquaternium", for example:

Polyquaternium-2 (Chemical Abstracts No. 63451-274, for example Mirapol® A-15)

Polyquaternium-5 (Copolymer of acrylamide and β-methacryloxyethyltrimethylammonium methosulphate, CAS No. 26006-224)

Polyquaternium-6 (Homopolymer of N,N-dimethyl-N-2-propenyl-2-propene-1-aminium chloride, CAS No. 26062-79-3, for example Merquat® 100

Polyquaternium-7 N,N-Dimethyl-N-2-propenyl-2-propene-1-aminium chloride, polymer with 2-propenamide, CAS No. 26590-05-6, for example Merquat® S Polyquaternium-10 Quaternary ammonium salt of hydroxyethylcellulose, CAS No. 53568-66-4, 55353-19-0, 54351-50-7, 68610-92-4, 81859-24-7, for example Celquat® SC-230M Polyquaternium-11 Vinylpyrrolidone/dimethylaminoethyl methacrylate copolymer/diethyl sulphate reaction product, CAS No. 53633-54-8, for example Gafquat 755N Polyquaternium-16 Vinylpyrrolidone/vinylimidazolinium methochloride copolymer, CAS No. 29297-55-0, for example Luviquat® HM 552

Polyquaternium-17 CAS No. 90624-75-2, for example Mirapol® AD-1

Polyquaternium-19 Quaternized water-soluble polyvinyl alcohol

Polyquaternium-20 Water-dispersible quaternized polyvinyl octadecyl ether

Polyquaternium-21 Polysiloxane-polydimethyl-dimethylammonium acetate copolymer, for example Abil® B 9905

Polyquaternium-22 Dimethyidiallylammonium chloride/acrylic acid copolymer, CAS No. 53694-7-0, for example Merquat® 280

Polyquaternium-24 Polymeric quaternary ammonium salt of hydroxyethylcellulose, reaction product with an epoxide substituted by lauryl dimethylammonium, CAS No. 107987-23-5, for example Quatrisoft® LM-200

Polyquaternium-28 Vinylpyrrolidone/methacrylamidopropyltrimethylammonium chloride copolymer, for example Gafquat® HS-100

Polyquaternium-29 For example Lexquat® CH

Polyquaternium-31 CAS No. 136505-02-7, for example Hypane QT 100

Polyquaternium-32 N,N,N-Trimethyl-2-[(2-methyl-1-oxo-2-propenyl)-oxy]ethaneaminium chloride, polymer with 2-propene-amide, CAS No. 35429-19-7

Polyquaternium-37 CAS No. 26161-33-1

Preparations according to the invention for hair care advantageously comprise 0.2–50% by weight of one or more film-forming agents, preferably 5–30% by weight, in particular 10–25% by weight, in each case based on the total weight of the preparations. Such embodiments of the preparations according to the invention care for hair damaged or worn out by environmental influences, or protect against such environmental influences. The preparations according to the invention furthermore impart to the hairstyle loose body and hold, without being tacky.

Where appropriate, it is possible and advantageous to use the preparations according to the invention as a base for pharmaceutical formulations. Mutatis mutandis, appropriate requirements apply to the formulation of medical preparations. The transitions between pure cosmetics and pure pharmaceuticals are continuous here. All active compound classes are in principle suitable according to the invention as pharmaceutical active compounds, liphophilic active compounds being preferred. Examples are: antihistamines, antiphlogistics, antibiotics, antimycotics, active compounds which promote circulation, keratolytics, hormones, steroids, vitamins and the like.

The cosmetic and dermatological preparations according to the invention can comprise cosmetic auxiliaries such as are usually used in such preparations, for example preservatives, bactericides, virucides, perfumes, substances for preventing foaming, dyestuffs, pigments which have a colouring action, other thickening agents which do not fall under the definition of the thickeners according to the invention, surface-active substances, emulsifiers, softening, humidifying and/or humectant substances, antiinflammatory substances, medicaments, fats, oils, waxes or other customary constituents of a cosmetic or dermatological formulation, such as alcohols, polyols, polymers, foam stabilizers, electrolytes and organic solvents.

Mixtures of the abovementioned solvents are particularly advantageously used.

Other constituents which can be used are fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids, alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

The objects set are achieved according to the invention.

Unless stated otherwise, all amounts, percentages or parts refer to the weight, in particular to the total weight of the preparations or of the respective mixture.

The following examples are intended to illustrate the present invention.

The amounts below refer to the weight or are percentages by weight.

Preparation Example for PEG-140-chol$_2$ 36 g (6 mmol) of polyethylene oxide (M=6,000 gmol$^{-1}$, n≈140) are dissolved in 50 ml of benzene and freed from traces of water present therein by freeze-drying. The polyethylene oxide is then taken up in 70 ml of freshly dehydrated dichloromethane. Under a nitrogen atmosphere, 10.8 g (24mmol) of cholesteryl chloroformate and 5 ml of pyridine (the latter distilled over CaH$_2$) are added. The

Preparation Example for PEG-180-chol$_2$ 48 g (6 mmol) of polyethylene oxide (M=8,000 gmol$^{-1}$, n≈180) are dissolved in 70 ml of benzene and freed from traces of water present therein by freeze-drying. The polyethylene oxide is then taken up in 100 ml of freshly dehydrated dichloromethane. Under a nitrogen atmosphere, 10.8 g (24 mmol) of cholesteryl chloroformate and 5 ml of pyridine (the latter distilled over CaH$_2$) are added. The polymer is precipitated in 1.5 l of diethyl ether and purified by repeated precipitation (three times) from dichloromethane/diethyl ether. The predried product is dissolved in ca.1 l of warm acetone and completely precipitates out at 0° C. Yield: 44 g of PEG-180-chol$_2$ (48 mmol), corresponding to 80% of theory.

Preparation Example for PEG-450-chol$_2$ 120 g (6 mmol) of polyethylene oxide (M=20,000 gmol$^{-1}$, n≈450) are dissolved in 170 ml of benzene and freed from traces of water present therein by freeze-drying. The polyethylene oxide is then taken up in 100 ml of freshly dehydrated dichloromethane. Under a nitrogen atmosphere, 10.8 g (24 mmol) of cholesteryl chloroformate and 5 ml of pyridine (the latter distilled over CaH$_2$) are added. The polymer is precipitated in 2.5 l of diethyl ether and purified by repeated precipitation (three times) from dichloromethane/diethyl ether. The predried product is dissolved in ca.1 l of warm acetone and completely precipitates out at 0° C.

Preparation Example for PEG-800-chol$_2$ 58 g (6 mmol) of polyethylene oxide (M=35,000 gmol$^{-1}$, n≈800) are dissolved in 130 ml of benzene and freed from traces of water present therein by freeze-drying. The polyethylene oxide is then taken up in 100 ml of freshly dehydrated dichloromethane. Under a nitrogen atmosphere, 10.8 g (24 mmol) of cholesteryl chloroformate and 5 ml of pyridine (the latter distilled over CaH$_2$) are added. The polymer is precipitated in 1.5 l of diethyl ether and purified by repeated precipitation (three times) from dichloromethane/diethyl ether. The predried product is dissolved in ca.1 l of warm acetone and completely precipitates out at 0° C.

Preparation Example for Cholesterol N-(6-isocyanatohexyl)carbamate (Compound 1)

78 g of cholesterol are dissolved with 48 ml of 1,6-hexyl diisocyanate in 200 ml of absolute toluene. After 4 ml of pyridine have been added, the solution is held at 80° C. for 48 h. All of the solvent is then distilled off, and the residue is taken up in 600 ml of petroleum ether (boiling range 40–60° C.) At −10° C. the product precipitates out. The precipitate is filtered off with suction, washed with more petroleum ether and then dried in an oil pump vacuum.

Preparation Example for Cholesteryl Polyacrylate 5 g of polyacrylic acid (M=450,000) and 5 ml of pyridine are dissolved in 150 ml of anhydrous N-methylpyrrolidone at 60° C. A solution of 0.555 g (1 mmol) of compound 1 in 10 ml of N-methylpyrrolidone is then added dropwise. The reaction mixture is stirred at 60° C. for 24 h and then precipitated with acetone. The material which precipitates out is added to ca. 100 ml of water, and 20–40 ml of sodium hydroxide solution (40% strength) are added. The gel is treated several times with acetone and then dried at 10 mbar. The resulting mass is dissolved in ca. 250 ml of water, precipitated out with methanol and dried in a diaphragm pump vacuum. This operation is repeated, and then drying is carried out for 24 h at a pressure of 10$^{-2}$ mbar.

Preparation Example for Cholesteryldextran 3 g of dextran and 0.2 g of 1 are reacted in the presence of 5 ml of pyridine in 80 ml of DMSO (8 h at 80° C.) After 500 ml of ethanol have been added, the product precipitates out at 0° C. Further purification is carried out by dialysis with water.

Preparation Example for Cholesterylhydroxyethylcellulose

Hydroxyethylcellulose is dried at 60° C. and a pressure of 10$^{-2}$ mbar for 24 h. A mixture of 2 g of dried hydroxyethylcellulose, 120 ml of anhydrous N-methylpyrrolidone and 30 ml of anhydrous pyridine is degassed and stirred at 60° C. for 38 h under argon 0.09 g (0.20 mmol) of cholesterol chloroformate in 7 ml of N-methylpyrrolidone is added to the pale yellow, high-viscosity solution. The mixture is stirred for 18 h at 60° C. under argon. The cholesterylhydroxyethylcellulose is precipitated in acetone and dried at 10 mbar. For further purification, the cholesterylhydroxyethylcellulose is extracted in a Soxhlet extractor using benzene for 24 h and then dried at 10$^{-2}$ mbar for 24 h.

Preparation Example for Stearylhydroxyethylcellulose

Hydroxyethylcellulose is dried at 60° C. and a pressure of 10$^{-2}$ mbar for 24 h. A mixture of 2 g of dried hydroxyethylcellulose, 120 ml of anhydrous N-methylpyrrolidone and 30 ml of anhydrous pyridine is degassed and stirred at 60° C. for 38 h under argon 0.06 g (0.20 mmol) of stearoyl chloride in 5 ml of N-methylpyrrolidone is added to the pale yellow, high-viscosity solution. The mixture is stirred for 24 h at 60° C. under argon. The stearylhydroxyethylcellulose is precipitated in acetone and dried at 10 mbar. The stearylhydroxyethylcellulose is dissolved in ca. 200 ml of water (stirring for 24 h), precipitated again from acetone and dried for 24 h at 10$^{-2}$ mbar.

Preparation Example for Oleylhydroxyethylcellulose

Hydroxyethylcellulose is dried at 60° C. and a pressure of 10$^{-2}$ mbar for 24 h. A mixture of 2 g of dried hydroxyethylcellulose, 120 ml of anhydrous N-methylpyrrolidone and 30 ml of anhydrous pyridine is degassed and stirred at 60° C. for 38 h under argon 0.06 g (0.20 mmol) of oleoyl chloride in 5 ml of N-methylpyrrolidone is added to the pale yellow, high-viscosity solution. The mixture is stirred for 24 h at 60° C. under argon. The oleylhydroxyethylcellulose is precipitated in acetone and dried at 10 mbar. The oleylhydroxyethylcellulose is dissolved in ca. 200 ml of water (stirring for 24 h), precipitated again from acetone and dried for 24 h at 10$^{-2}$ mbar.

Preparation Example for Palmitylhydroxyethylcellulose

Hydroxyethylcellulose is dried at 60° C. and a pressure of 10$^{-2}$ mbar for 24 h. A mixture of 2 g of dried polymer is precipitated in 1.5 l of diethyl ether and purified by repeated precipitation (three times) from dichloromethane/diethyl ether. The predried product is dissolved in ca1 l of warm acetone and completely precipitates out at 0° C.

hydroxyethylcellulose, 120 ml of anhydrous N-methylpyrrolidone and 30 ml of anhydrous pyridine is degassed and stirred at 60° C. for 38 h under argon 0.05 g (0.20 mmol) of palmityl chloride in 5 ml of N-methylpyrrolidone is added to the pale yellow, high-viscosity solution. The mixture is stirred for 24 h at 60° C. under argon. The palmitylhydroxyethylcellulose is precipitated in acetone and dried at 10 mbar. The palmitylhydroxyethylcellulose is dissolved in ca. 200 ml of water (stirring for 24 h), precipitated again from acetone and dried for 24 h at $10^{-2}$ mbar.

Preparation Example for Dodecyl Polyacrylate 5 g of polyacrylic acid (M=450,000) and a spatula tip of 4-dimethylaminopyridine are dissolved in 150 ml of anhydrous N-methylpyrrolidone at 60° C. A solution of 0.389 g (210 mmol) of dodecylamine and 0.475 g (2.30 mmol) of N,N'-dicyclohexylcarbodiimide in 10 ml of N-methylpyrrolidone is then added dropwise. The reaction mixture is stirred at 60° C. for 24 h and then precipitated out with acetone. The compound which precipitates out is added to ca. 100 ml of water, and 20–40 ml of sodium hydroxide solution (40%) are added. The gel is treated several times with acetone and then dried at 10 mbar. The resulting mass is dissolved in ca. 250 ml of water, precipitated out with methanol and dried in a diaphragm pump vacuum. This operation is repeated, and drying is then carried out at a pressure of 10 mbar for 24 h.

Preparation Example for Stearoyl Polyacrylate 5 g of polyacrylic acid (M=450,000) and a spatula tip of 4-dimethylaminopyridine are dissolved in 150 ml of anhydrous N-methylpyrrolidone at 60° C. A solution of 0.566 g (2.10 mmol) of stearylamine and 0.475 g (2.30 mmol) of N,N'-dicyclohexylcarbodiimide in 10 ml of N-methylpyrrolidone is then added dropwise. The reaction mixture is stirred at 60° C. for 24 h and then precipitated out with acetone. The compound which precipitates out is added to ca. 100 ml of water, and 20–40 ml of sodium hydroxide solution (40%) are added. The gel is treated several times with acetone and then dried at 10 mbar. The resulting mass is dissolved in ca. 250 ml of water, precipitated out with methanol and dried in a diaphragm pump vacuum. This operation is repeated, and drying is then carried out at a pressure of 10 mbar for 24 h.

Preparation Example for PEG-800 Diglycyrrhetinyl Stearate 10 g of glycyrrhetinyl stearate are refluxed with 10 g of $K_2CO_3$ (anhydrous) in 50 ml of $SOCl_2$ for ca. 1 h. Excess $SOCl_2$ is stripped off in a water-pump vacuum, and the residue is taken up in 150 ml of boiling hexane and filtered whilst hot. The filtrate is evaporated to dryness, and the product is dried for 3 h using an oil pump. The resulting acid chloride is used without further purifications.

The reaction (and work-up) with 40 g of PEG (35,000 gmol$^{-1}$) is carried out in a manner analogous to the corresponding instructions for cholesteryl chloroformate.

Preparation Example for PEG-800 Diazelate

The reaction of PEG (35,000 g mol$^{-1}$) with azelaoyl chloride is carried out in a manner analogous to the instructions for cholesteryl chloroformate. To hydrolyze the free carbonyl chloride groups, the polymer is stirred for 24 h in a 95:5 acetone:water mixture.

Preparation Example for PEG-800 Diretinate 44 g (1.26 mmol) of anhydrous PEG (35,000 gmol$^{-1}$) are stirred with 3.02 g (10 mmol) of retinoic acid, 2.08 g (10 mmol) of dicyclohexylcarbodiimide and 12 mg (0.1 mmol) of dimethylaminopyridine in 100 ml of absolute $CH_2Cl_2$ under an $N_2$ atmosphere for 12 h at room temperature. For purification, the polymer is precipitated out 3 times in 1.5 l of diethyl ether in each case, twice in 1.5 l of petroleum ether (boiling range 40–60° C.) in each case and then recrystallized twice from ca. 1 l of acetone. The product is freed from traces of solvent by freeze-drying from benzene.

Polyvinyl Alcohol Modified with Stearic Acid: Stearyl Polyvinyl Alcohol 5 g of polyvinyl alcohol (M=250,000) and a spatula tip of 4-dimethylaminopyridine are dissolved in 150 ml of anhydrous N-methylpyrrolidone at 60° C. A solution of 0.5 g of stearic acid and 0.475 g of N,N'-dicyclohexylcarbodiimide in 10 ml of N-methylpyrrolidone is then added dropwise. The reaction mixture is stirred at 60° C. for 24 h, and then precipitated out with acetone. The polymer is precipitated 3 times from methanol. The resulting mass is dried for 48 h at a pressure of $10^{-2}$ mbar.

Yield: 42 g

Copolymer of Methacrylic Acid Glucosamide and Cholesteryl Methacrylate

The solution of 5 g (20.2 mmol) of methacrylic acid glucosamide, 0.046 g (0.1 mmol) of cholesteryl methacrylate and 7 mg of AIBN in 50 ml of tetrahydrofuran and 15 ml of water (deionized) is stirred at 60° C. for 48 h. The mixture is precipitated from 700 ml of acetone. The product, dried in a diaphragm pump vacuum, is dissolved in ca. 50 ml of water, and the insoluble constituents are removed by centrifugation. The solution is again precipitated and dried at a pressure of $10^{-2}$ mbar.

Yield: 48 g

Copolymer of Polyvinylpyrrolidone and Cholesteryl Methacrylate 15 g (134.94 mmol) of vinylpyrrolidone, 0.5 g (1.10 mmol) of cholesteryl methacrylate and 100 mg of AIBN are added to 150 ml of ethanol (96%, dest.). The suspension is degassed and stirred under argon for 18 h at 60° C. The reaction mixture is precipitated from 2 l of ether. The material is dissolved in chloroform and again precipitated from ether. (Repeat the operation 2–3 times). Drying under reduced pressure gives 13.4 g.

Cholesteryl Methacrylate

A solution of 6 ml of methacryloyl chloride in 30 ml of dichloromethane is added dropwise to 20 g (51.72 mmol) of cholesterol and 8 ml of triethylamine in 170 ml of dichloromethane (abs.). The mixture is stirred overnight at room temperature. The solvent is distilled off under reduced pressure, and the residue is recrystallized three times from the ca. 400 ml of ethanol (95%). Drying is carried out at a pressure of $10^{-2}$ mbar for 24 h Yield: 12.2 g Methacrylic Acid Glucosamide 80 ml of a freshly prepared 15 M sodium methoxide solution are added to a suspension of 25 g of glucosamine hydrochloride in 100 ml of methanol (abs.) at an internal temperature of 4–10° C. A total of 20 ml of methacryloyl chloride in 1 ml portions, alternating with sodium methoxide solution, are then added at a rate such that the pH following addition of the sodium methoxide solution is again between 8 and 9.

The suspension is introduced into 1.5 l of petroleum ether (30/70), and the precipitate is filtered off with suction and dried in a diaphragm pump vacuum. The solid is refluxed in ca. 250 ml of methanol and filtered with suction whilst hot. It is stored overnight in a freezer, filtered off with suction and dried under reduced pressure: 10.1 g

Preparation Examples for POE Esters (Triblock Copolymers)

40 g of polyoxyethylene (POE; 1.1 mmol, M=35,000 g/mol) were weighed into a 1 liter flask and predried over a course of about 30 h using an oil pump under reduced pressure ($9.3 \times 10^{-5}$ bar). The polymer was then dissolved in 50 ml of benzene at elevated temperature to give a highly viscous, clear solution and then rapidly frozen in liquid nitrogen. The frozen polymer solution was freeze-dried over the course of about 45 h under reduced pressure. The benzene, which forms an azeotropic mixture with the residual water, was removed by sublimation. The dried POE was then dissolved in 1 dl of abs. methylene chloride under a nitrogen atmosphere.

The triblock copolymers A, F and H were synthesized by esterification of POE with a carbonyl chloride, and triblock copolymers B, C, D and G were synthesized by esterification of POE with a carboxylic acid.

The synthesis of triblock copolymer A

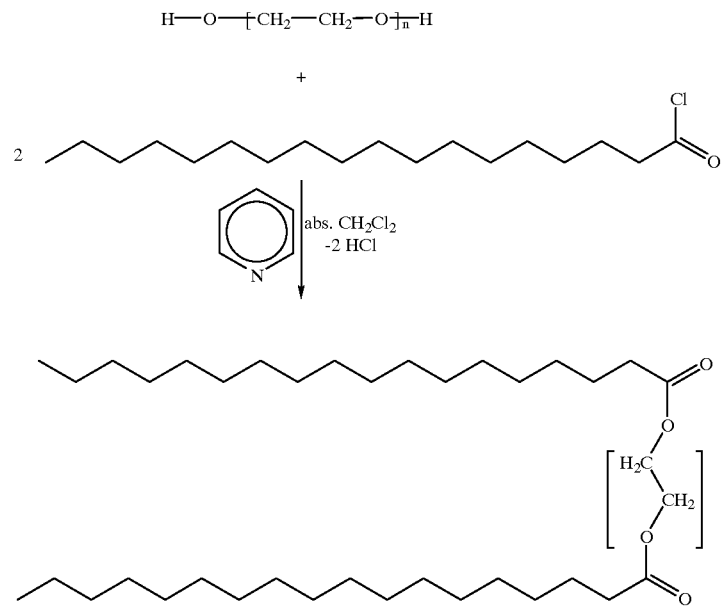

The synthesis of triblock copolymer F

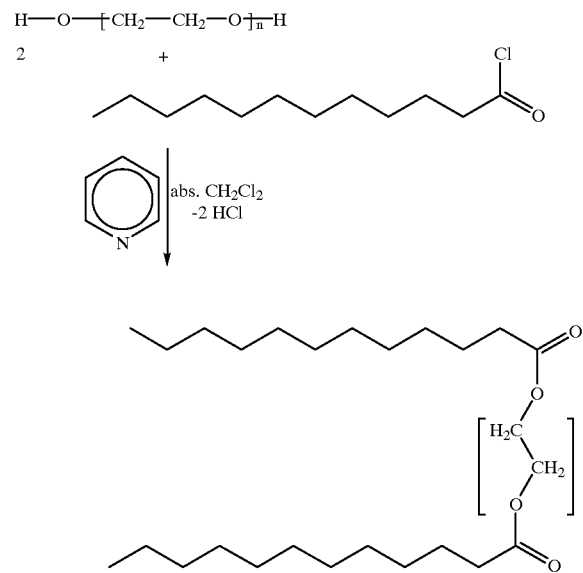

The synthesis of triblock copolymer B
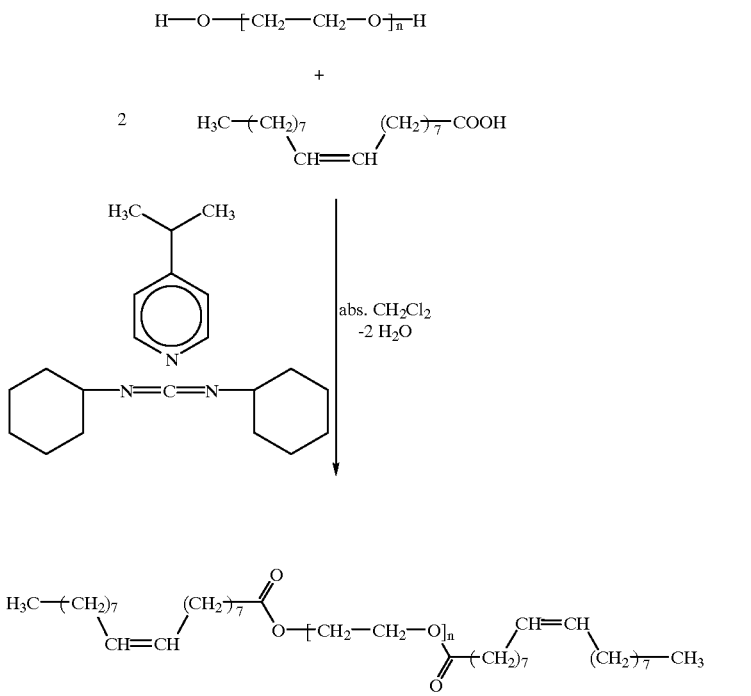
The synthesis of triblock copolymer C
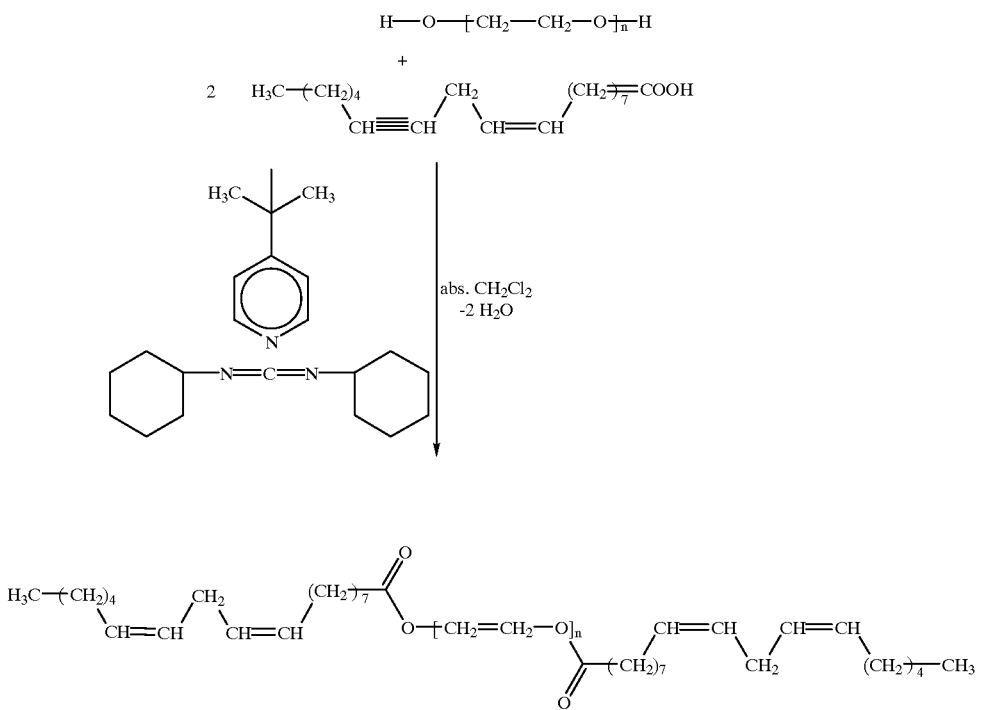

-continued
The synthesis of triblock copolymer D

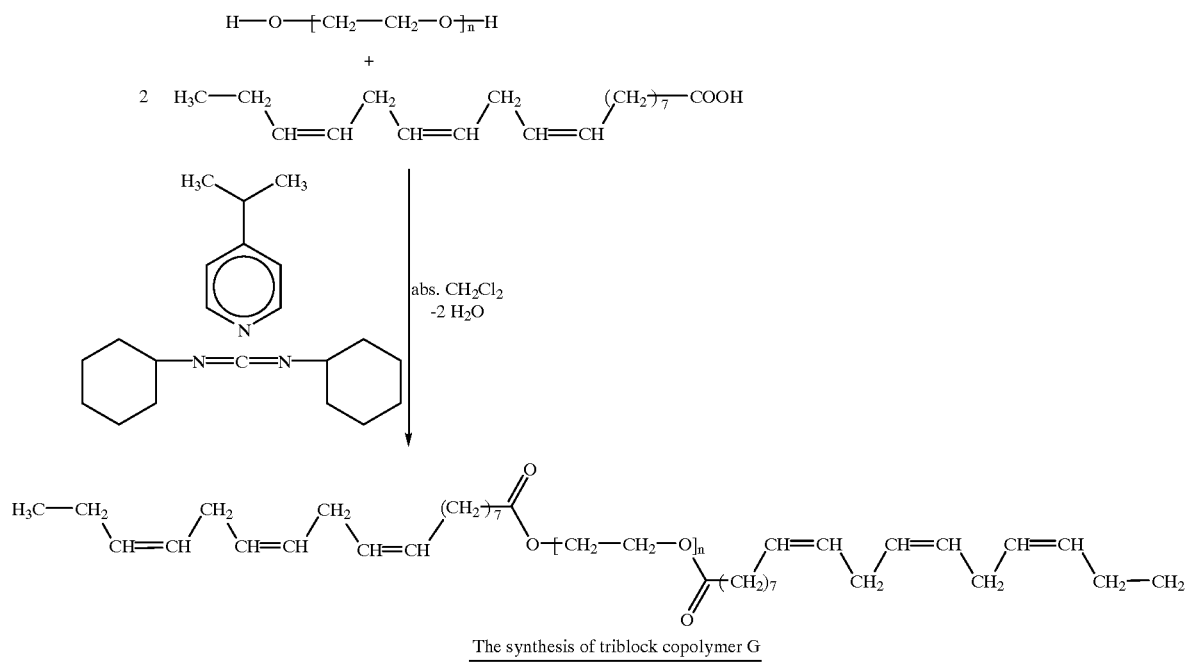

The synthesis of triblock copolymer G

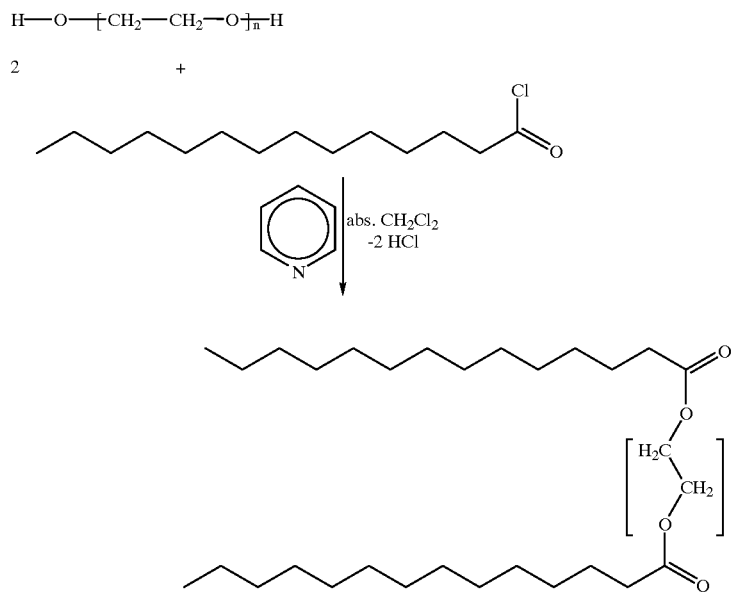

After the POE had been dissolved in 1 dl of abs. methylene chloride, 7 g of the corresponding carboxylic acid (≈30 mmol, in excess), 4.6 g of DCC and 3 ml (spatula tip) of dimethylaminopyridine were added under a nitrogen atmosphere. The reaction mixture was left to react at room temperature with vigorous stirring for 15 h.

The solutions of all of the triblock copolymers A–H were then discharged into a dropping funnel and precipitated out three times in 15 l of diethyl ether in each case and twice in 1.5 l of petroleum ether in each case with slow dropwise addition and vigorous stirring. The precipitate was then filtered off and evaporated to dryness by rotating on a rotary evaporator. The dried triblock copolymer was dissolved in 0.5 l of acetone at elevated temperature until a clear solution was formed, and recrystallized at −20° C. over the course of three hours in order to remove the polar impurities. The polymer was then filtered off, precipitated out in 1.5 l of petroleum ether and recrystallized again in 0.5 l of acetone.

The triblock copolymer was then precipitated out again in 1.5 l of diethyl ether and 1.5 l of petroleum ether, filtered and evaporated to dryness by rotating on a rotary evaporator. The fine white powder was dissolved in 1 dl of benzene with slight warming until a clear solution was visible, frozen in liquid nitrogen and freeze-dried using an oil pump under reduced pressure over the course of ca. 45 h.

Example 1
Base for foaming shaving gel; face-care gel

| | |
|---|---|
| Lecithin (Phospholipon 90) | 0.600 |
| Sodium lauroyl lactylate | 6.000 |
| PEG-150 distearate | 1.000 |
| Dicaprylyl ether | 5.000 |
| Glycerol | 5.000 |
| Antioxidants, water (aqua) | ad 100 |

Example 2
Body-care gel

| | |
|---|---|
| Polyglyceryl-3 diisostearate | 1.600 |
| Sodium lauroyl lactylate | 2.800 |
| Lauryl glucoside | 5.600 |
| Dicaprylyl ether | 5.000 |
| Glycerol | 5.000 |
| PEG-150 distearate | 2.000 |
| Water (aqua) | ad 100 |

Example 3
Shower gel

| | |
|---|---|
| Polyglyceryl-3 diisostearate | 1.000 |
| Sodium caproyl lactylate | 3.100 |
| Lauroyl glucoside | 6.200 |
| Dicaprylyl ether | 5.000 |
| Propylene glycol | 5.000 |
| PEG-300 pentaerythrityl tetraisostearate | 2.000 |
| Water (aqua) | ad 100 |

Example 4
Aftershave gel

| | |
|---|---|
| Glyceryl isostearate | 1.200 |
| Sodium lauroyl lactylate | 3.000 |
| Lauryl glucoside | 6.000 |
| Dicaprylyl ether | 5.000 |
| Butylene glycol | 5.000 |
| PEG-200 hydrogenated glyceryl palmitate | 1.000 |
| Water (aqua) | ad 100 |

Example 5
Hair gel

| | |
|---|---|
| Glyceryl oleate | 2.000 |
| Sodium lauroyl lactylate | 6.000 |
| Butylene glycol | 4.000 |
| Dicaprylyl ether | 5.000 |
| Glycerol | 1.000 |
| Cetylhydroxyethylcellulose | 2.000 |
| Water (aqua) | ad 100 |

Example 6
Make-up remover gel

| | |
|---|---|
| Diglyceryl monoisostearate | 1.200 |
| Sodium lauroyl lactylate | 6.000 |
| Dicaprylyl ether | 5.000 |
| Butylene glycol | 5.000 |
| PEG-230 glyceryl triisostearate | 2.000 |
| Water (aqua) | ad 100 |

Example 7
Shaving gel base

| | |
|---|---|
| Diglycerol diisostearate | 1.200 |
| Sodium lauroyl lactylate | 3.000 |
| Lauryl glucoside | 6.000 |
| Dicaprylyl ether | 5.000 |
| Butylene glycol | 5.000 |
| PEG-800 diglycyrrhetinyl stearate | 2.000 |
| Water (aqua) | ad 100 |

Example 8
Cleansing gel

| | |
|---|---|
| Sodium isostearoyl actylate | 2.400 |
| Sodium lauroyl lactylate | 4.800 |
| Dicaprylyl ether | 5.000 |
| Propylene glycol | 3.000 |
| Stearyl polyvinyl alcohol | 2.000 |
| Water (aqua) | ad 100 |

Example 9
Sunscreen gel

| | |
|---|---|
| Decaglyceryl monooleate | 5.300 |
| Glyceryl monocaprylate | 1.800 |
| Tridecyl isononanoate | 3.000 |
| Eusolex 232 | 2.000 |
| Cyclomethicone | 3.000 |
| Glycerol | 5.000 |
| Cholesteryl polyacrylate | 2.000 |
| Water (aqua) | ad 100 |

Example 10
Face-cleansing gel

| | |
|---|---|
| Glyceryl isostearate | 1.833 |
| Polyglyceryl laurate | 5.333 |
| Dodecyl polyacrylate | 2.000 |
| Octyl isostearate | 3.333 |
| Cyclomethicone | 3.333 |
| Glycerol | 5.000 |
| Methylparaben | 0.250 |
| Water (aqua) | ad 100 |

Example 11
Face-cleansing gel

| | |
|---|---|
| 2-Ethylhexyl glycerol ether | 1.800 |
| Sodium lauroyl lactylate | 5.400 |
| PEG-150 distearate | 2.000 |
| Dicaprylyl ether | 5.000 |
| Butylene glycol | 5.000 |
| Water (aqua) | ad 100 |

Example 12
Gel base for wound treatment

| | |
|---|---|
| Lecithin (Epicuron 200) | 0.600 |
| Sodium lauroyl lactylate | 4.000 |
| PEG-150 distearate | 2.000 |
| Dicaprylyl ether | 5.000 |
| Glycerol | 5.900 |
| Antioxidants, water (aqua) | ad 100 |

Example 13
Deodorant gel

| | |
|---|---|
| Sodium lauroyl lactylate | 1.800 |
| Cholesteryl hydroxyethylcellulose distearate | 2.000 |
| Dicaprylyl ether | 5.000 |
| Glyceryl caprylate | 5.400 |
| Butylene glycol | 5.000 |
| Water (aqua) | ad 100 |

Example 14
Base for shaving foam

| | |
|---|---|
| Methylglucose isostearate | 1.200 |
| Lauryl glycoside | 6.000 |
| PEG-800 dioleate | 2.000 |
| Dicaprylyl ether | 5.000 |
| Sodium lauroyl lactylate | 3.000 |
| Butylene glycol | 5.000 |
| Water (aqua) | ad 100 |

Example 15
Eye make-up remover gel

| | |
|---|---|
| Polyglyceryl-3 diisostearate | 1.600 |
| Sodium lauroyl lactylate | 2.800 |
| Lauryl glucoside | 5.600 |
| Dicaprylyl ether | 5.000 |
| Glycerol | 5.000 |
| PEG-800 Chol$_2$ | 2.000 |
| Water (aqua) | ad 100 |

Example 16

| | |
|---|---|
| Sodium lauroyl lactylate | 5.400 |
| Glycerol caprate | 1.800 |
| PEG-800 distearate | 2.000 |
| Dicaprylyl ether | 5.000 |
| Butylene glycol | 5.000 |
| Water (aqua) | ad 100 |

-continued

Example 17

| | |
|---|---|
| Polyglyceryl methylglucose distearate | 1.200 |
| Sodium lauroyl lactylate | 6.000 |
| PEG-800 distearate | 2.000 |
| Dicaprylyl ether | 5.000 |
| Butylene glycol | 5.000 |
| Water (aqua) | ad 100 |

Example 18

| | |
|---|---|
| Lauryl glycoside | 6.400 |
| Sodium lauroyl lactylate | 3.200 |
| PEG-800 distearate | 2.000 |
| Dicaprylyl ether | 5.000 |
| Lauryl glycol | 0.800 |
| Butylene glycol | 5.000 |
| Water (aqua) | ad 100 |

Example 19

| | |
|---|---|
| 2-Ethylhexylglycerol ether | 0.600 |
| Sodium lauroyl sarcosinate | 6.000 |
| PEG-800 distearate | 2.000 |
| Dicaprylyl ether | 5.000 |
| Butylene glycol | 5.000 |
| Water (aqua) | ad 100 |

Example 20

| | |
|---|---|
| Sodium cocoyl glutamate | 0.260 |
| PEG-800 distearate | 2.000 |
| Glyceryl caprylate | 6.960 |
| Dicaprylyl ether | 5.000 |
| Butylene glycol | 5.000 |
| Water (aqua) | ad 100 |

Example 21

| | |
|---|---|
| Sodium cocoyl glutamate | 0.130 |
| PEG-800 distearate | 2.000 |
| Glyceryl caprylate | 6.960 |
| Dicaprylyl ether | 5.000 |
| Lauryl glycoside | 0.260 |
| Butylene glycol | 5.000 |
| Water (aqua) | ad 100 |

Example 22
Spray gel

| | |
|---|---|
| Lecithin (Phospholipon 90) | 6.100 |
| PEG-800 distearate | 3.200 |
| Ethanol | 21.800 |
| Dicaprylyl ether | 1.000 |
| Water (aqua) | ad 100 |

Example 23
Base for aerosol spray

| | |
|---|---|
| Lecithin (Phospholipon 90) | 6.800 |
| PEG-800 distearate | 2.800 |
| Ethanol | 24.000 |
| Cetearyl isononanoate | 0.900 |
| Water (aqua) | ad 100 |

Example 24
Base for shaving gel, shaving foam, hair-care product

| | |
|---|---|
| Lecithin (Phospholipon 90) | 6.900 |
| PEG-800 distearate | 3.000 |
| Ethanol | 23.400 |
| Caprylic/capric triglycerides | 1.700 |
| Water (aqua) | ad 100 |

Example 25

| | |
|---|---|
| Glyceryl laurate | 2.400 |
| Sucrose laurate (Sisterna) L70-C, 40% strength solution | 12.000 |
| Dicaprylyl ether | 5.000 |
| Butylene glycol | 3.000 |
| PEG-150 distearate | 1.000 |
| Water (aqua) | ad 100 |

What is claimed is:

1. Oil-in-water microemulsion gels,
    (a) which comprise
        a discontinuous oil phase and a continuous aqueous phase,
        one or more oil-in-water emulsifiers which do not contain ethylene oxide or propylene oxide and
        optionally furthermore comprising one or more water-in-oil emulsifiers
        having an emulsifier content of less than 20% by weight, based on the total weight of the microemulsion, and which is formed
        by formulating a mixture of the base components, comprising the aqueous phase, the oil phase, one or more of said oil-in-water emulsifiers, optionally one or more water-in-oil emulsifiers, and optionally further auxiliaries, additives and/or active compounds, to form a microemulsion,
    (b) in which the droplets of the discontinuous oil phase are joined to one another by one or more crosslinking substances, the molecules of which have at least one hydrophilic region, which has an extension sufficient to bridge the distance between the microemulsion droplets, and at least one hydrophobic region, which enters into a hydrophobic interaction with the microemulsion droplets.

2. Microemulsion gels according to claim 1, wherein said oil-in-water emulsifier is selected from the group consisting of acyl lactylates, glutamates, sarcosinates, isethionates, sulphosuccinates, alaninates, amphoacetates, polyglycerol esters, alkylglycosides, alkylpolyglycosides, sorbitan esters, methylglucose esters, esters of hydroxy acids, and polyglycerol methylglucose esters.

3. Oil-in-water microemulsion gels,
    (a) which comprise
        a discontinuous oil phase and a continuous aqueous phase,
        comprising:
            one or more oil-in-water emulsifiers which do not contain ethylene oxide or propylene oxide,
            lecithin or lecithin derivatives, and
            optionally furthermore comprising one or more water-in-oil emulsifiers
            having an emulsifier content of less than 20% by weight, based on the total weight of the microemulsion, which are formed
            by slowly adding water to a mixture of the base components, comprising the oil phase, one or more of said oil-in-water emulsifiers and lecithin, optionally one or more water-in-oil emulsifiers, and optionally further auxiliaries, additives and/or active compounds, such that an intermediate gel is formed which, on the addition of more water, leads to a microemulsion,
    (b) in which the droplets of the discontinuous oil phase are joined to one another by one or more crosslinking substances, the molecules of which have at least one hydrophilic region, which has an extension sufficient to bridge the distance between the microemulsion droplets, and at least one hydrophobic region, which enters into a hydrophobic interaction with the microemulsion droplets.

4. Method of crosslinking or thickening oil-in-water microemulsions having a discontinuous oil phase and a continuous aqueous phase which comprises joining the droplets of the discontinuous oil phase of said microemulsions to one another by one or more crosslinking substances, the molecules of which have at least one hydrophilic region, which has an extension sufficient to bridge the distance between the microemulsion droplets, and at least one hydrophobic region, which enters into a hydrophobic interaction with the microemulsion droplets.

5. Oil-in-water microemulsions, which comprise an oil phase and an aqueous phase comprising:
- one or more oil-in-water emulsifiers which do not contain ethylene oxide or propylene oxide and
- optionally one or more water-in-oil emulsifiers
- having an emulsifier content of less than 20% by weight, based on the total weight of the microemulsion, which is formed
- by formulating a mixture of the base components, comprising the aqueous phase, the oil phase, one or more of said oil-in-water emulsifiers, optionally one or more water-in-oil emulsifiers, and optionally further auxiliaries, additives and/or active compounds, to form a microemulsion.

6. Oil-in-water microemulsions according to claim 5, wherein
- said at least one oil-in-water emulsifier is selected from the group consisting of acyl lactylates, glutamates, sarcosinates, isethionates, sulphosuccinates, alaninates, amphoacetates, polyglycerol esters, alkylglycosides, alkylpolyglycosides, sorbitan esters, methylglucose esters, esters of hydroxy acids, and polyglycerol methylglucose esters.

7. Oil-in-water microemulsions, which comprise a discontinuous oil phase and a continuous aqueous phase, comprising:
- one or more oil-in-water emulsifiers which do not contain ethylene oxide or propylene oxide,
- lecithin or lecithin derivatives, and
- optionally furthermore comprising one or more water-in-oil emulsifiers
- having an emulsifier content of less than 20% by weight, based on the total weight of the microemulsion, which is formed
- by slowly adding water to a mixture of the base components, comprising the oil phase, one or more of said oil-in-water emulsifiers and lecithin, optionally one or more water-in-oil emulsifiers, and optionally further auxiliaries, additives and/or active compounds, such that an intermediate gel is formed which, on the addition of more water, leads to a microemulsion.

* * * * *

UNITED STATES PATENT AND TRADEMARK OFFICE
CERTIFICATE OF CORRECTION

PATENT NO. : 6,468,551 B1
DATED : October 22, 2002
INVENTOR(S) : Khiet Hien Diec et al.

It is certified that error appears in the above-identified patent and that said Letters Patent is hereby corrected as shown below:

<u>Title page,</u>
Item [56], References Cited, U.S. PATENT DOCUMENTS;
1st. entry, change date from "3/1995" to -- 3/1993 --
2nd. entry, change date from "5/1998" to -- 2/1996 --
3rd. entry, change date from "12/1999" to -- 11/1995 --

Signed and Sealed this

Third Day of June, 2003

JAMES E. ROGAN
*Director of the United States Patent and Trademark Office*